United States Patent
Ellis et al.

(10) Patent No.: US 10,000,453 B2
(45) Date of Patent: Jun. 19, 2018

(54) CHELATION DIRECTED C—H ACTIVATION REACTIONS CATALYZED BY SOLID-SUPPORTED PALLADIUM(II) CATALYSTS

(71) Applicant: VIRGINIA COMMONWEALTH UNIVERSITY, Richmond, VA (US)

(72) Inventors: Keith C. Ellis, Midlothian, VA (US); Frank B. Gupton, Midlothian, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days. days.

(21) Appl. No.: 15/532,828

(22) PCT Filed: Dec. 3, 2015

(86) PCT No.: PCT/US2015/063598
§ 371 (c)(1),
(2) Date: Jun. 2, 2017

(87) PCT Pub. No.: WO2016/090078
PCT Pub. Date: Jun. 9, 2016

(65) Prior Publication Data
US 2017/0362181 A1 Dec. 21, 2017

Related U.S. Application Data

(60) Provisional application No. 62/088,198, filed on Dec. 5, 2014.

(51) Int. Cl.
*C07D 211/84* (2006.01)
*C07D 221/10* (2006.01)
(Continued)

(52) U.S. Cl.
CPC .......... *C07D 221/10* (2013.01); *B01J 21/185* (2013.01); *B01J 23/44* (2013.01); *C07C 249/04* (2013.01);
(Continued)

(58) Field of Classification Search
CPC .. C07D 221/10; C07D 213/26; C07D 215/06; C07D 213/30; C07C 249/04; C07C 2602/10; B01J 21/185; B01J 23/44
(Continued)

(56) References Cited

U.S. PATENT DOCUMENTS

2002/0193641 A1 12/2002 Borredon et al.
2009/0076266 A1 3/2009 Daugulis et al.
(Continued)

*Primary Examiner* — Taylor V Oh
(74) *Attorney, Agent, or Firm* — Whitham, Curtis & Cook, P.C.

(57) ABSTRACT

Chelation directed C—H activation reactions that are catalyzed by Pd(11) on Multi-Walled Carbon Nanotubes (MW-CNT), Single-Walled Carbon Nanotubes (SWCNT), or graphene are provided. The reactions are used to directly and regioselectively or regiospecifically functionalize specific C—H bonds, e.g. to build complexity into small molecules. Features and advantages of the present invention will be set forth in the description of invention that follows, and in part will be apparent from the description or may be learned by practice of the invention. The invention will be realized and attained by the compositions and methods particularly pointed out in the written description and claims hereof.

18 Claims, 11 Drawing Sheets

| Oxidant | FG |
|---|---|
| PhI(OAc)₂ | OAc/OR |
| NCS/NBS/NIS | Cl/Br/I |
| (Ar-I⁺-Mes)BF₄⁻ | Ph/Ar |
| PhI=NTs | N |
| pyridinyl-F⁺BF₄⁻ | F |
| (dibenzothiophenium-CF₃ BF₄⁻) | CF₃ |

(51) Int. Cl.
  *B01J 23/44*   (2006.01)
  *B01J 21/18*   (2006.01)
  *C07D 215/06*  (2006.01)
  *C07D 213/30*  (2006.01)
  *C07D 213/26*  (2006.01)
  *C07C 249/04*  (2006.01)

(52) U.S. Cl.
  CPC ......... *C07D 213/26* (2013.01); *C07D 213/30* (2013.01); *C07D 215/06* (2013.01); *C07C 2602/10* (2017.05)

(58) Field of Classification Search
  USPC ........................................................ 546/346
  See application file for complete search history.

(56) References Cited

U.S. PATENT DOCUMENTS

| | | |
|---|---|---|
| 2012/0059179 A1 | 3/2012 | Yu |
| 2013/0211106 A1 | 8/2013 | El-Shall et al. |

A.
Pd(OAc)$_2$ +
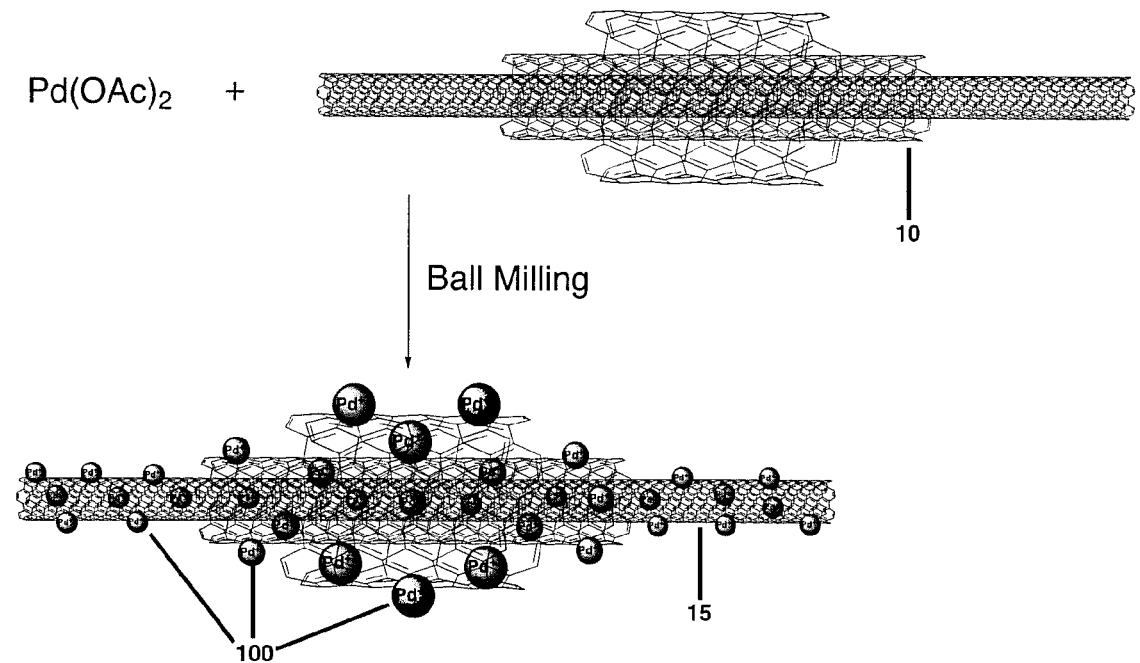
B.
Pd(OAc)$_2$ +
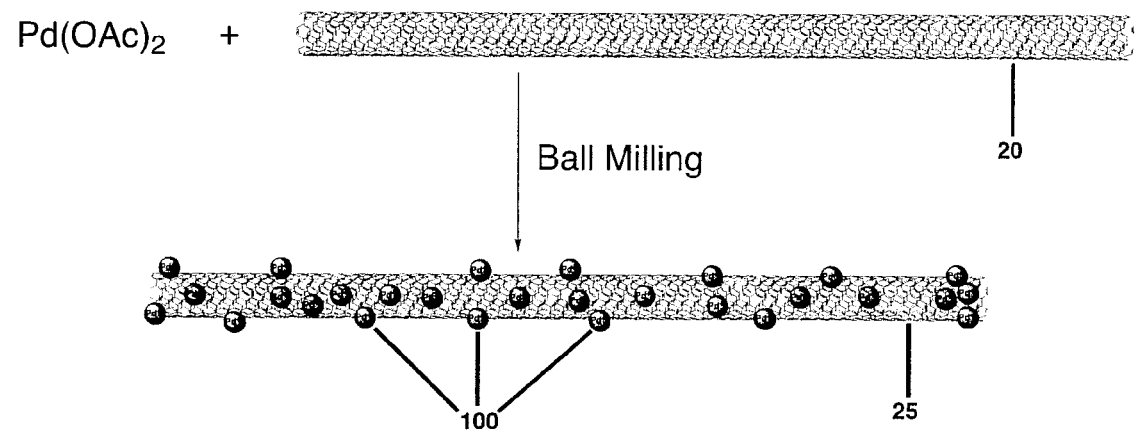
Figure 2A and B

General Substrate Model

Het = sp$^2$-hybridized N or O heteroatom

C = sp$^2$- or sp$^3$-hybridized carbon atom substituted in the reaction

H = hydrogen atom removed in the reaction $n$ = 1, 2, or 3 atoms

A.
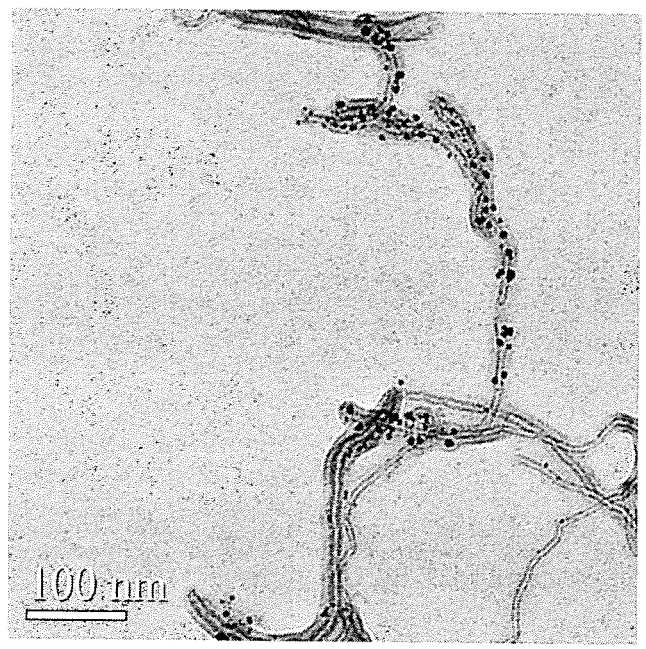
B.
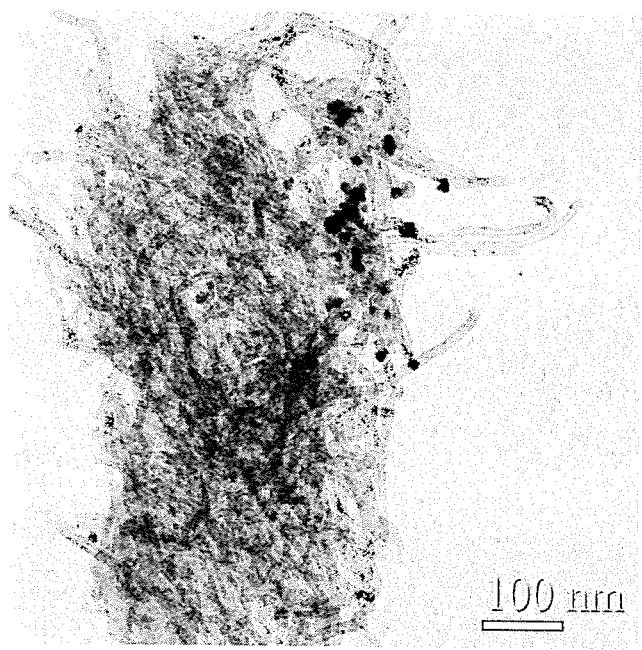
Figure 9A and B

CHELATION DIRECTED C—H ACTIVATION REACTIONS CATALYZED BY SOLID-SUPPORTED PALLADIUM(II) CATALYSTS

CROSS-REFERENCE TO RELATED APPLICATIONS

This application claims benefit of U.S. provisional patent applications 62/088,198, filed Dec. 5, 2014, the complete contents of which is hereby incorporated by reference.

BACKGROUND OF THE INVENTION

Field of the Invention

The invention provides chelation-directed C—H activation reactions that are catalyzed by Pd(II) on carbon-based solid supports including Multi-Walled Carbon Nanotubes (MWCNTs), Single-Walled Carbon Nanotubes (SWCNTs), and graphene. In particular, the reactions are used to directly and regioselectively or regiospecifically functionalize specific C—H bonds, e.g. in order to build complexity into small molecules.

Background

C—H activation chemistry has emerged as a new and important area of organic chemistry methodology development. The selective, direct functionalization of a specific C—H bond is the most atom-economical route to build complexity into small molecules. One method to achieve selectivity in C—H activation chemistry is to use palladium catalysis combined with an intramolecular directing group, such as a pyridinyl or other basic nitrogen functional group. Examples of selective C—H to C—O,[1] C-halogen,[1a,2] C—C,[3] C—N,[4] C—F,[5] and C—CF$_3$[6] transformations using N-chelation-directed palladium catalysis have been reported in the literature.

While there are extensive examples of N-chelation-directed C—H activation reactions using homogeneous Pd(II) sources, no examples of this reaction utilize a solid-supported Pd(II) catalyst. There is a need in the art for improved selective C—H activation reaction methodologies.

SUMMARY OF THE INVENTION

Features and advantages of the present invention will be set forth in the description of invention that follows, and in part will be apparent from the description or may be learned by practice of the invention. The invention will be realized and attained by the compositions and methods particularly pointed out in the written description and claims hereof.

Novel chelation-directed reactions which result in the specific or selective reaction of a C—H group in a substrate molecule or compound of interest are described herein. The reactions result in replacement or substitution of the H atom of the C—H group by a different atom or functional group of interest in a regioselective or regiospecific manner. The reactions are catalyzed by a solid-supported Pd catalyst, for example Pd(II) on Multi-Walled Carbon Nanotubes [Pd(II)/MWCNTs], which undergo a Pd(II)/Pd(IV) catalytic cycle. Solid-supported catalysts as contemplated in this invention have several advantages including: 1) ease of catalyst recovery, 2) eliminating or reducing palladium contamination in the products following the reaction, and 3) the ability to recycle catalyst and reuse it multiple times.

These catalysts are advantageous because they are easily recovered after reactions, leave behind low or no Pd contamination in products following a reaction, and can be recycled and reused multiple times with no or minimal loss of activity. As described herein, Pd(II) solid-supported catalysts including Pd(II)/MWCNT, Pd(II)/SWCNT, and Pd(II)/graphene are used to catalyze a wide variety of substitution reactions such as C—H to C—O, C-halogen, C—C, C—N, C—C-halogen, etc. Further, the presently described reactions require much shorter times than do comparable reactions catalyzed by homogeneous Pd catalysts.

It is an object of this invention to Provide a method for selectively producing functionalized aryl or heteroaryl compounds. The method comprises the steps of: combining an aryl or heteroaryl compound containing at least one C—H group with a solid-supported Pd(II) catalyst selected from the group consisting of Pd(II)/MWCNT, Pd(II)/SWCNT and Pd(II)/graphene, wherein the combining is performed under conditions wherein the solid-supported Pd(II) catalyst selectively catalyzes a reaction which attaches a functional group to the aryl or heteroaryl compound at the at least one C—H group as a reaction product; and separating the solid-supported Pd(II) catalyst from said reaction product. In some aspects, the method further comprises the steps of recovering the solid-supported Pd(II) catalyst after the separating step; and repeating the steps of combining and separating using at least some of the solid-supported Pd(II) catalyst recovered in the recovering step.

The invention also provides a solid-supported Pd(II) catalysts selected from the group consisting of Pd(II)/MWNCT, Pd(II)/SWCNT and Pd(II)/graphene, wherein the solid-supported Pd(II) catalysts are present as a powder or a dispersion in a fluid and wherein the solid-supported Pd(II) catalysts have a purity with respect to Pd(0) or Pd(IV) species of at least 90%. For example, the catalyst may have a purity of at least about 90, 91, 92, 93, 94, 95, 96, 97, 98, 99 or even 100%.

The invention further provides a method of catalyzing a reaction which functionalizes specific C—H bonds in small molecules, comprising the step of: combining a first molecule of interest having at least one specific C—H bond with a solid-supported Pd(II) catalyst under conditions which activate the at least one specific C—H bond for replacement of the H atom of the at least one specific C—H bond with a different atom or a functional group of interest to produce a second molecule of interest which is identical to the first molecule of interest except for the replacement of the H atom with the different atom or functional group of interest. In some aspects, the first molecule of interest and the second molecule of interest each contain at least one aryl or heteroaryl moiety. In other aspects, the first molecule of interest and the second molecule of interest each contain at least one substituted or unsubstituted pyridine. In yet other aspects, the first molecule of interest and the second molecule of interest each contain at least one substituted or unsubstituted phenyl. In additional aspects, the first molecule of interest and the second molecule of interest each contain at least one substituted or unsubstituted phenyl. In other aspects, the first molecule of interest and the second molecule of interest each contain at least one substituted or unsubstituted cycloalkyl. In yet further aspects, the first molecule of interest and the second molecule of interest each contain at least a second substituted or unsubstituted phenyl. In additional aspects, the first molecule of interest and the second molecule of interest each contain at least one substituted or unsubstituted pyridine. In aspects of the invention, the different atom is a halogen. In other aspects, the functional group of interest is a substituted or unsubstituted alkyl or aryl moiety. In further aspects, the functional group of interest is an ether or ester. In yet further aspects, the functional group of interest is an ether OR, where R is a substituted or unsubstituted alkyl or alkaryl moiety of 1 to 25 carbons. In additional aspects, the heterogenous Pd(II) catalyst is Pd(II)/MWNCT, Pd(II)/SW-CNT, or Pd(II)/graphene.

BRIEF DESCRIPTION OF THE DRAWINGS

FIG. 2A-C. Schematic depictions of a Pd(II)/multiwalled carbon nanotube catalyst (Pd(II)/MWCNT) (A); a Pd(II)/single-walled carbon nanotube catalyst (Pd(II)/SWCNT) (B); and a Pd(II)/graphene sheet catalyst (C).

FIGS. 9A and B. TEM images of the Pd(II)/MWCNT catalyst before (A) and after (B) use in a C—H activation reaction.

DETAILED DESCRIPTION

Figure 1:
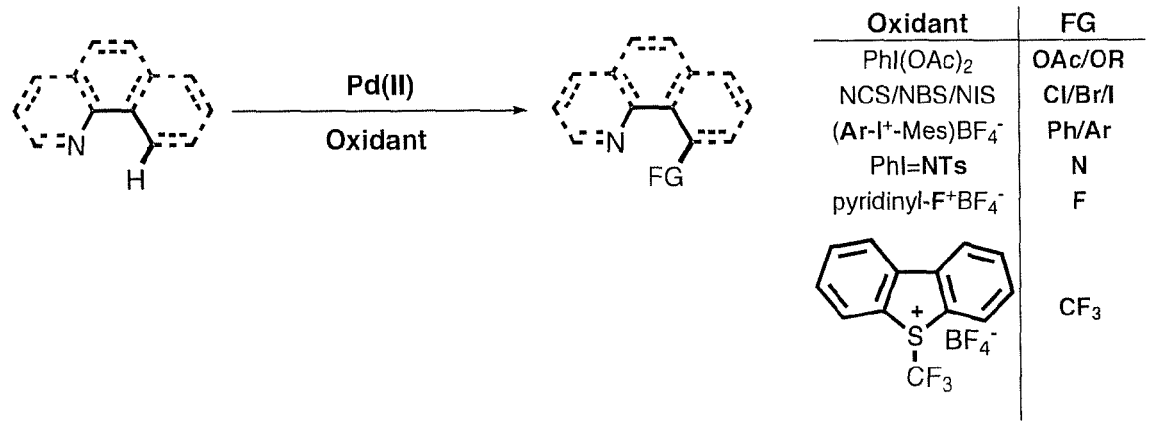
FIG. 1. General reaction for oxidative Pd(II)-catalyzed chelation-directed C—H activation reactions to install a functional group (FG), showing exemplary oxidants and exemplary FGs.
Figure 2C:
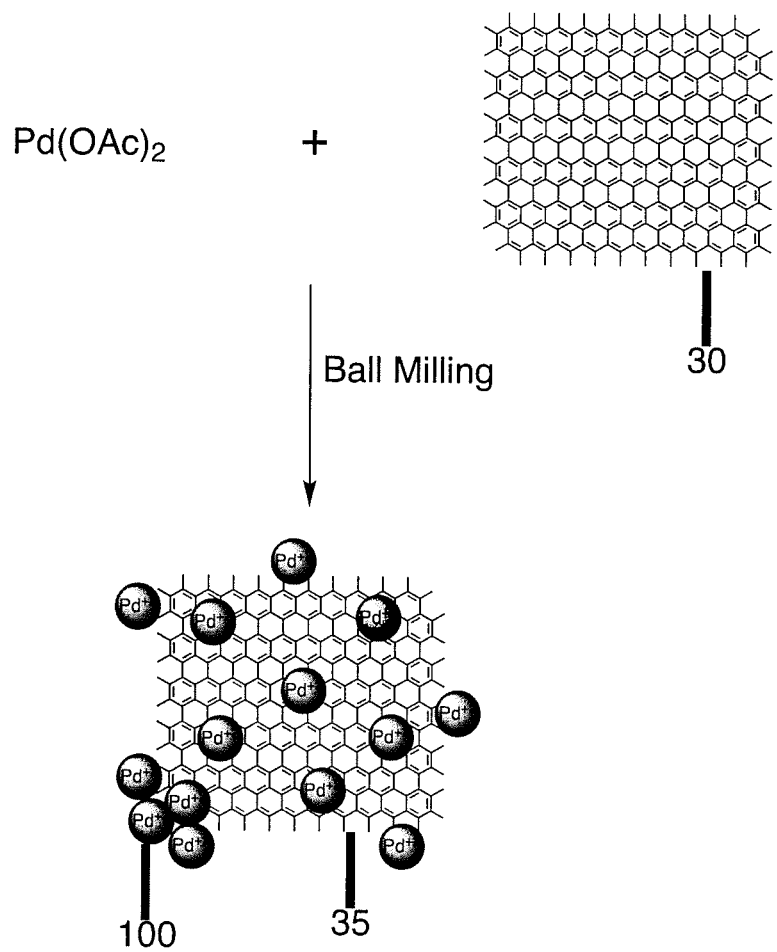
Figure 3:
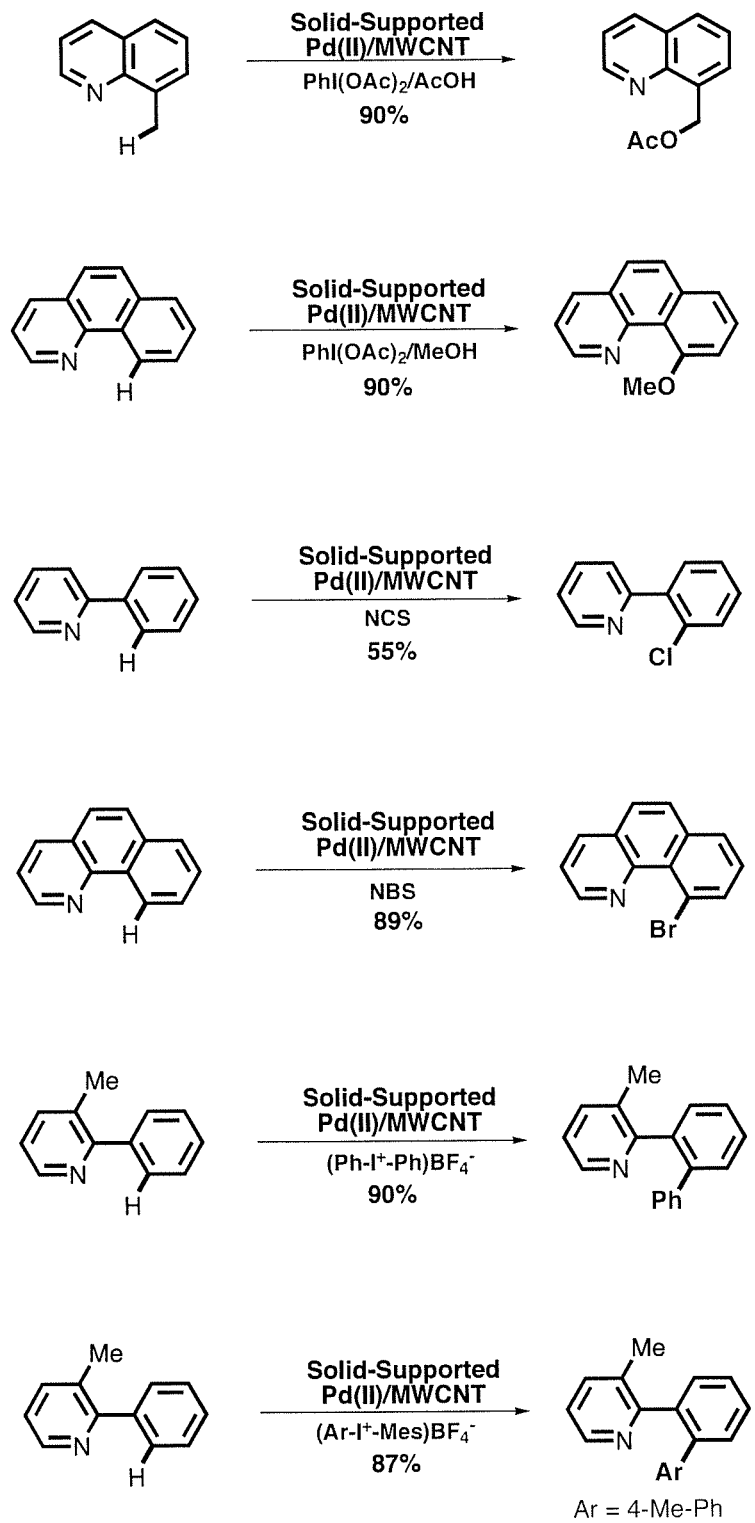
FIG. 3. Exemplary regioselective reactions catalyzed by Pd(II)/MWCNTs.
Figure 4:
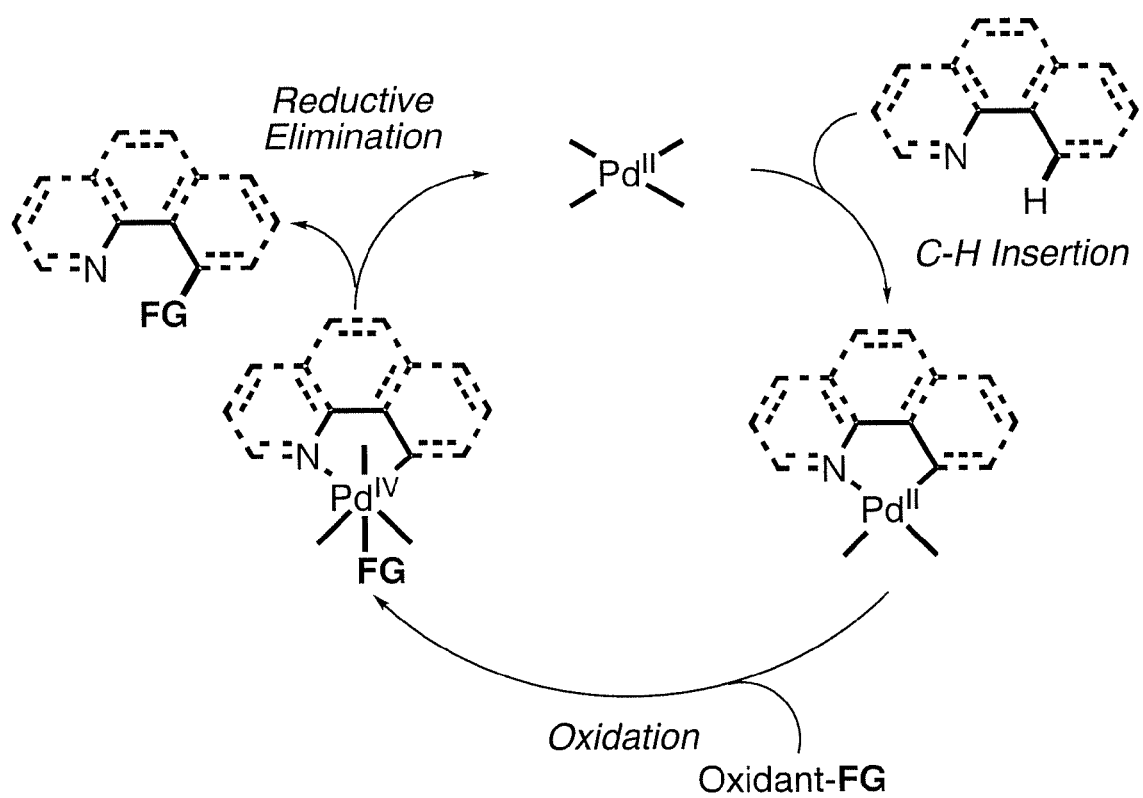
FIG. 4. Mechanism of Pd(II)/Pd(IV) catalyzed chelation-directed C—H activation reactions.

The invention provides novel reactions for substituting an H atom of a C—H group in a substrate molecule of interest with a different atom or group of atoms (functional group, FG) of interest (FIG. 1). The chelation-directed C—H activation/substitution reactions are catalyzed using solid-supported Pd(II) catalysts in which the Pd(II) is positioned or supported on multiwalled carbon nanotubes [i.e. Pd(II) on Multi-Walled Carbon Nanotubes or Pd(II)/MWCNTs], single-walled carbon nanotubes [i.e. Pd(II) on Single-Walled Carbon Nanotubes or Pd(II)/SWCNTs], or graphene [i.e. Pd(II) on graphene or Pd(II)/graphene] (FIG. 2A-C). These catalysts are referred to herein as solid-supported catalysts. As an example of the utility of the invention, in the presence of Pd(II)/MWCNT, H is lost from the C—H group and the C and a second atom of the substrate serve as ligands to chelate Pd(II) (FIG. 3). As described below, the second chelating atom is part of a "directing group" that is present in the substrate molecule. Thus, a first chelation adduct is formed which comprises the substrate molecule and Pd(II) chelated by C and the second chelating atom (FIG. 4). Under oxidizing conditions, contact with an oxidant species bearing an atom or functional group (FG) results in loss of the atom or FG from the oxidant species and formation of a second chelation adduct in which Pd, in the form of Pd(IV), is chelated by the C and second chelating atom of the substrate, and also by the atom or FG from the oxidant species. Subsequently, the Pd(IV) intermediate undergoes a reductive elimination, returning to the Pd(II) state and a new covalent bond is made between C and the atom or FG from the oxidant species, thereby forming a modified substrate molecule, which is eliminated from the adduct. In sum, the H of C—H in the substrate is ultimately replaced by a different atom or FG and the resulting modified (functionalized) substrate molecule is released from the adduct concomitant with regeneration of the Pd(II) catalyst. The use of solid supported Pd(II)/MWCNT as the catalyst permits facile recovery of the catalyst from the reaction mixture (e.g. by filtration) with little or no residual catalyst left behind in the product, and the catalyst can thus be reused in other reactions.

All of the solid-supported catalysts described herein are prepared using a similar method. The different catalysts—Pd(II)/MWCNTs, Pd(II)/SWCNTs, or Pd(II)/graphene—are prepared simply by varying the carbon-based solid support (MWCNTs, SWCNTs, or graphene) used in the catalyst synthesis. The general method to prepare the catalyst(s) is to combine a salt of palladium(II) (such as palladium acetate), the carbon-based solid support (such as MWCNTs, SWCNTs, or graphene), and a grinding ball in a ball mill and shaking for up to about 10 minutes, e.g. about 1, 2, 3, 4, 5, 6, 7, 8, or 9 minutes. The resulting solid is collected and used directly in the C—H activation reactions.

In order to obtain solid-supported catalysts containing predominantly palladium (II), milling times under about 15 minutes (e.g. less than about 14, 13, 12, 11, or 10 minutes, and preferably under about 10 minutes) are required. Longer milling times (over about 15 minutes) give solid-supported catalysts composed of predominantly Pd(0).

In general, the C—H activation reactions are carried out by mixing the solid-supported Pd(II) catalyst, a substrate, and an oxidant in a compatible solvent and heating the mixture to the appropriate temperature until the reactions are complete. The nature of the oxidant defines the FG that is installed in the substrate as well as the solvent and temperature that are required. Once the reaction is complete, the solid-supported catalyst is removed by filtration and very little Pd metal is left behind (<250 ppb). Other suitable separation techniques may be used, but filtration offers a low cost and effective option. The byproduct (the reduced form of the oxidant) can be removed by any of several methods including acid-base washing and/or column chromatography. Following these steps, the purified, selectively functionalized product of the reaction can be isolated by evaporation.

The Pd(II) purity of the catalysts with respect to other Pd species (such as Pd(0) or Pd(IV)) is at least 75%-100%. For example, the catalyst may have a purity of at least about 75, 80, 85, 90, 95 or 100%, including all integers and decimal fractions in between, to at least 0.1%.

The general mechanism of C—H activation is depicted in FIG. 4 where "FG" stands for "functional group", which is installed using various oxidants, examples of which are presented in FIG. 1. Exemplary reactions as described herein are depicted in FIG. 3, where the second chelating atom is an $sp^2$-hybridized nitrogen (N) which is present in a pyridine directing group. However, as described in detail below, these are only a few illustrative aspects of the invention, as other directing groups comprising other atoms, other substrates, and other oxidants that install different FGs may also be employed.

Significantly, these reactions occur regiospecifically or regioselectively, i.e. when multiple C—H groups are present in the original C—H bearing molecule, the substitution is preferentially made at only one predefined C—H in the molecule, but not at other C—H groups (a regiospecific reaction), or at least is made to a greater extent at the one predefined C—H (a regioselective reaction). These reactions are thus very useful in manufacturing particular molecules of interest in high yield and purity, for example, small molecules which are drugs or are used in manufacturing drugs and other commercial products of interest.

Figure 5:
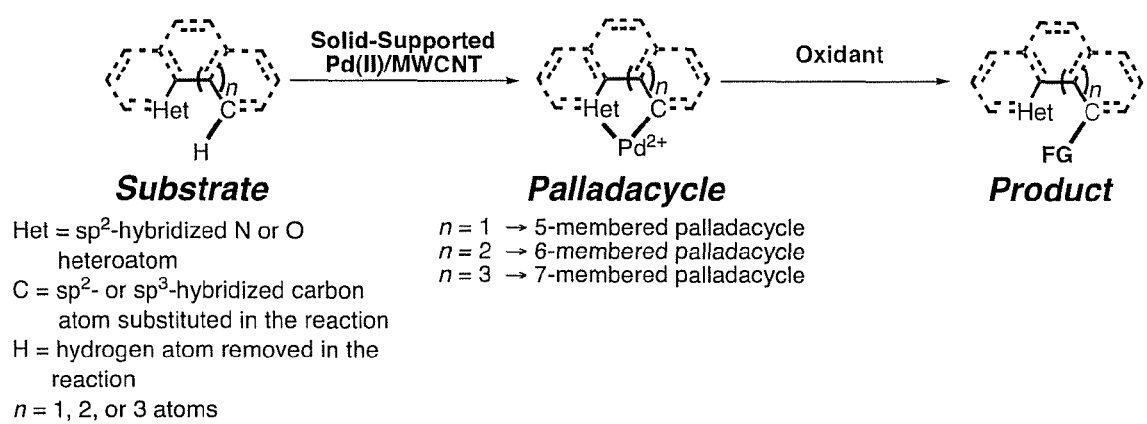
FIG. 5. Structural requirements for Pd(II)-catalyzed chelation-directed C—H activation substrates, the relationship between the functionalized C—H group and the directing group, and the palladacycle intermediates.

As described above, the reactions provided herein are chelation-directed reactions, that is the specificity of the reaction depends upon and/or is the result of the ability of the C—H group and a second atom in the molecule of interest to successfully form a Pd(II) chelate (FIG. 5). Generally, the C—H group and the second chelating atom are located in substrate molecules that have a significant electronic and/or steric bias for palladation at a particular C—H. Such C—H groups typically have the following characteristics: a carbon atom that is $sp^2$ or $sp^3$ hybridized (Substrate, FIG. 5), have the second chelating atom of the directing group separated from the carbon of the C—H group by 2 to 4 atoms (Substrate, FIG. 5), and are of such a structure that the carbon atom of the C—H group and the second chelating atom can form 5-, 6- or 7-membered palladacycles with Pd(II) (Palladacycle, FIG. 5).

Generally, the second atom is a heteroatom that is part of a chelation-directing group within the substrate molecule (FIG. 5). Exemplary directing groups which comprise the atoms and which are contained in a substrate molecule include but are not limited to: pyridine, quinoline, benzo[h]quinoline, imidazole, isoquinoline, tetrazole, pyrimidine, pyrazine, pyrazole, azobenzene, imine, indole, indoline, pyrrole, pyrrolidinone, oxime ether and actate, isoxazoline, various amide derivatives including but not limited to pivalamide, acyl benzylamine, acyl phenylethylamine, acyl aryl amine, acyl aniline, carboxylic acids, oxazolines, oxazolidinone, dihydroisoxazole, oxazole, benzofuran, anisole, dihydrofuran, anilides, acetanilide, amindoquinolines, and any other heterocycle or carbonyl derivative containing an $sp^2$-hybridized nitrogen or oxygen atom correctly positioned to form palladacycles similar to those in FIG. 5 and derivatives or molecular species which comprise these directing groups. Exemplary atoms of the directing groups that function as described herein include but are not limited to: $sp^2$-hybridized Nitrogen (e.g. N of pyridine, pyrazine, etc.) or Oxygen (e.g. O of a carbonyl (C=O) group) atoms.

The C—H group and the additional or second atom of the substrate molecule that chelates Pd(II) must be stereochemically positioned within the molecule so as to permit successful Pd(II) chelation and adduct formation (palladation). In general, the C of the C—H group and the second chelating atom must be separated by 2 to 4 atoms and be positioned relative to each other such that the carbon atom of the C—H group (Substrate, FIG. 5) and the second chelating atom can form 5-, 6-, or 7-membered palladacycles with Pd(II) (Palladacycle, FIG. 5). The substrates that are acted upon are generally small molecules, e.g. molecules with a molecular weight of less than about 1000 daltons, and usually less than about 900 daltons.

Figure 6:
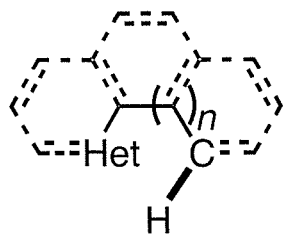
FIG. 6. A General Model for Substrates that undergo Chelation-Directed C—H Activation Reactions with Solid-Supported Pd(II) catalysts.
Figure 7:
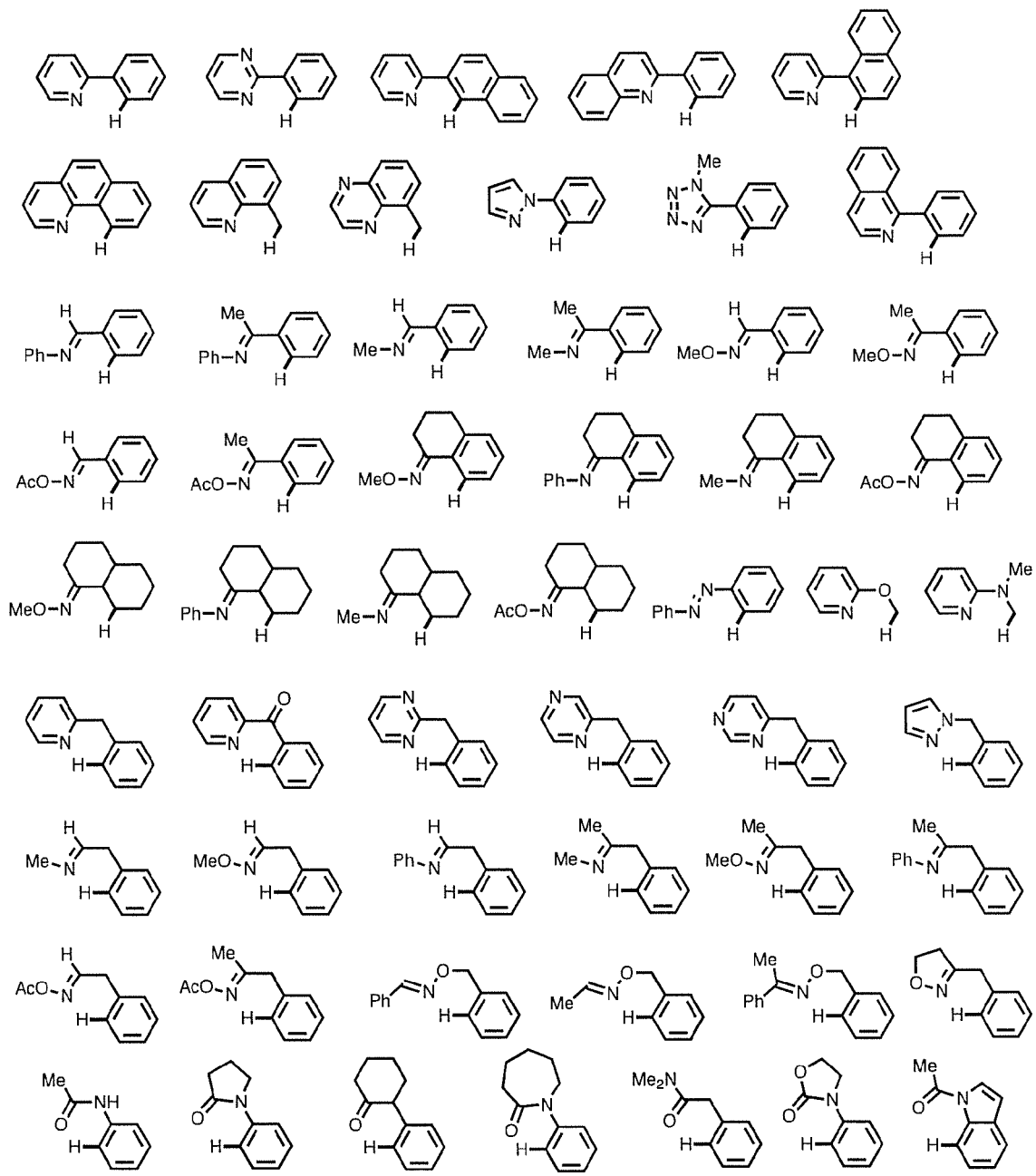
FIG. 7. Examples of Substrates for Pd(II)-Catalyzed Chelation-Directed C—H Activation Reactions.

Exemplary substrate molecules that comprise suitable C—H groups and chelation directing groups capable of reacting as described herein conform to the general substrate model shown in FIG. 6. Examples of exemplary substrates are shown in FIG. 7 and include but are not limited to: 2-phenylpyridine, 2-phenylpyrimidine, 2-(naphthalen-2-yl) pyridine, 2-phenylquinoline, 2-(naphthalen-1-yl)pyridine, benzo[h]quinoline, 8-methylquinoline, 5-methylquinoxaline, 1-phenyl-1H-pyrazole, 1-methyl-5-phenyl-1H-tetrazole, 1-phenylisoquinoline, N-benzylideneaniline, N-(1-phenylethylidene)aniline, N-benzylidenemethanamine, N-(1-phenylethylidene)methanamine, benzaldehyde O-methyl oxime, acetophenone O-methyl oxime, benzaldehyde O-acetyl oxime, acetophenone O-acetyl oxime, 3,4-dihydronaphthalen-1(2H)-one O-methyl oxime, N-(3,4-dihydronaphthalen-1(2H)-ylidene)aniline, N-(3,4-dihydronaphthalen-1(2H)-ylidene)methanamine, 3,4-dihydronaphthalen-1(2H)-one O-acetyl oxime, octahydronaphthalen-1(2H)-one O-methyl oxime, N-(octahydronaphthalen-1(2H)-ylidene)aniline, N-(octahydronaphthalen-1(2H)-ylidene)methanamine, octahydronaphthalen-1(2H)-one O-acetyl oxime, 1,2-diphenyldiazene, 2-methoxypyridine, N,N-dimethylpyridin-2-amine, 2-benzylpyridine, phenyl(pyridin-2-yl)methanone, 2-benzylpyrimidine, 2-benzylpyrazine, 4-benzylpyrimidine, 1-benzyl-1H-pyrazole, N-(2-phenylethylidene)methanamine, 2-phenylacetaldehyde O-methyl oxime, N-(2-phenylethylidene)aniline, N-(1-phenylpropan-2-ylidene)methanamine, 1-phenylpropan-2-one O-methyl oxime, N-(1-phenylpropan-2-ylidene)aniline, 2-phenylacetaldehyde O-acetyl oxime, 1-phenylpropan-2-one O-acetyl oxime, benzaldehyde O-benzyl oxime, acetaldehyde O-benzyl oxime, acetophenone O-benzyl oxime, 3-benzyl-4,5-dihydroisoxazole, N-phenylacetamide, 1-phenylpyrrolidin-2-one, 2-phenylcyclohexanone, 1-phenylazepan-2-one, N,N-dimethyl-2-phenylacetamide, 3-phenyloxazolidin-2-one, 1-(1H-indol-1-yl) ethanone as well an any derivative or analogue of these basic scaffold and any more complex molecule that contains these example scaffolds or which conform to the general substrate model (FIG. 6).

As described herein, solid-supported Pd(II) catalysis, e.g. Pd(II)/MWCNT, permits the selective conversion of a C—H group in a substrate molecule to C-FG (FIG. 1), where FG represents an atom, a group of atoms or a functional group of interest that is installed at the C. For example, in some aspects, FG=C, O, N, a halogen (e.g. F, Cl, Br, I), $CF_3$, etc. In other aspects, FG=a group of atoms, e.g. C—Z, where Z represents C, O, N, S, a halogen (e.g. F, Cl, Br, I), etc.; O—Z, where Z represents C or N, etc.; N—Z, where Z represents C, O, N, etc. In other aspects, FG=a functional group or molecule of interest attached to carbon including phenyl rings or substituted phenyl rings, aryl ring or substituted aryl rings, heteroaryl rings (such as pyridine, pyrimidine, pyrazine, pyrazole, azobenzene, imine, indole, pyrrole, pyrrolidinone, oxime ether and actate, isoxazoline, various amide derivatives, carboxylic acids, oxazolines, anilides, amindoquinolines) or substituted version of these heteroaryl rings, alkenyl groups or substituted alkenyl groups, alkynyl groups or substituted alkynyl groups; a functional group or molecule of interest attached to oxygen including alcohols substituted with alkyl groups and substituted alkyl group, alkenyl groups and substituted alkenyl groups, phenyl rings or substituted phenyl rings, aryl ring or substituted aryl rings, heteroaryl rings (such as pyridine, pyrimidine, pyrazine, pyrazole, azobenzene, imine, indole, pyrrole, pyrrolidinone, oxime ether and actate, isoxazoline, various amide derivatives, carboxylic acids, oxazolines, anilides, amindoquinolines) or substituted version of these heteroaryl rings, a functional group or molecule of interest attached to oxygen including esters substituted with alkyl groups and substituted alkyl group, alkenyl groups and substituted alkenyl groups, phenyl rings or substituted phenyl rings, aryl ring or substituted aryl rings, heteroaryl rings (such as pyridine, pyrimidine, pyrazine, pyrazole, azobenzene, imine, indole, pyrrole, pyrrolidinone, oxime ether and actate, isoxazoline, various amide derivatives, carboxylic acids, oxazolines, anilides, amindoquinolines) or substituted version of these heteroaryl rings; a functional group or molecule of interest attached to nitrogen including amines substituted with alkyl groups and substituted alkyl group, alkenyl groups and substituted alkenyl groups, phenyl rings or substituted phenyl rings, aryl ring or substituted aryl rings, heteroaryl rings (such as pyridine, pyrimidine, pyrazine, pyrazole, azobenzene, imine, indole, pyrrole, pyrrolidinone, oxime ether and actate, isoxazoline, various amide derivatives, carboxylic acids, oxazolines, anilides, amindoquinolines) or substituted version of these heteroaryl rings, a functional group or molecule of interest attached to nitrogen including amides substituted with alkyl groups and substituted alkyl group, alkenyl groups and substituted alkenyl groups, phenyl rings or substituted phenyl rings, aryl ring or substituted aryl rings, heteroaryl rings (such as pyridine, pyrimidine, pyrazine, pyrazole, azobenzene, imine, indole, pyrrole, pyrrolidinone, oxime ether and actate, isoxazoline, various amide derivatives, carboxylic acids, oxazolines, anilides, amindoquinolines) or substituted version of these heteroaryl rings; a functional group or molecule of interest attached to carbon including trifluoromethyl, trichloromethyl, tribromomethyl, and triiodomethyl, etc.

Exemplary oxidant species (molecules, compounds, etc.) which bear suitable "FG" atoms or functional groups that can replace H of a C—H group as described herein (FIG. 1) include but are not limited to: iodine (I) oxidants, peroxide oxidants, iodine(III) oxidants including $PhI(OAc)_2$ with carboxylic acids, especially acetic acid and trifluoroacetic acid; $PhI(OAc)_2$ with alcohols, especially 2-10 carbon alcohols and/or straight-chain alcohols that do not cause steric hindrance such as methanol, ethanol, propanol, etc; iodine(III)-based oxidative arylating agents $[Ph_2I]BF_4$ and [Ar—I-Mesityl]$BF_4$ where Ar are para-, meta-, or ortho-substituted aryl ring and the substitutens can be electronically neutral, electron-donating, or electron-withdrawing; oxidative amination reagents including [N-(p-toluenesulfonyl)imino]phenyliodinane and potassium persulfate with amides; electrophilic oxidative halogenating agents such as N-bromosuccinimide, N-chlorosuccinimide, N-iodosuccinimide; electrophilic oxidative fluorinating reagents including N-fluoro-pyridinium tetrafluoroborate, N-fluoro-2,4,6-trimethylpyridinium tetrafluoroborate, 1-chloromethyl-4-fluoro-1,4-diazoniabicyclo[2.2.2]octane bis (tetrafluoroborate), N-fluorobenzenesulfonimide; and oxidative trifluoromethylation reagents including 1,3-dihydro-3,3-dimethyl-1-(trifluoromethyl)-1,2-benziodoxole, 1-trifluoromethyl-1,2-benziodoxol-3-(1H)-one, 5-(Trifluoromethyl)dibenzothiophenium tetrafluoroborate, and 5-(trifluoromethyl)dibenzothiophenium trifluoromethanesulfonate Exemplary solid-supported catalysts that contain Pd(II) and can catalyze chelation-directed C—H activation reactions, such as Pd(II)/MWCNT, Pd(II)/SWCNT and Pd(II)/graphene, are shown in schematic illustrations in FIGS. 2A-C, respectively. These catalysts are all prepared using a ball milling process. FIG. 2A depicts multi-walled carbon nanotubes (MWCNT) 10 undergoing ball milling, during which Pd(II) atoms 100 are deposited on surfaces of MWCNT 10, to form Pd(II) catalyst Pd(II)/MWCNT 15. Similarly, FIG. 2B depicts single-walled carbon nanotube (SWCNT) 20 undergoing ball milling, during which Pd(II) atoms 100 are deposited on surfaces of SWCNT 20, to form Pd(II) catalyst Pd(II)/SWCNT 25. Finally, FIG. 2C depicts graphene 30 undergoing ball milling, during which Pd(II) atoms 100 are deposited on surfaces of graphene 30, to form Pd(II) catalyst Pd(II)/graphene 35.

In an exemplary embodiment, the solid-supported Pd(II) catalyst (e.g. Pd(II)/MWCNT) utilized in the reactions was prepared as follows: Palladium (II) acetate (0.103 g, 4.6 mmol) and multi-walled carbon nanotubes (0.500 g) were loaded in a 45 ml zirconia grinding vial. Two 12.77 mm diameter zirconia balls were also placed in the vial before sealing. The container was then placed in an 8000 M Spex Mixer/Mill. The contents in the mixer were shaken back and forth 5.9 cm and side-to-side 2.5 cm for 10 minutes at room temperature at 115 volts (1060 cycles/minute). The resulting solid was collected and used directly in reactions.

Those of skill in the art will recognize that these reaction conditions may be varied and still produce the present solid-supported catalysts. For example, the amount of Pd(II) (e.g. Pd(II) acetate or other Pd(II) salt) that is reacted can range from about 1 mmol to about 100 mmol (e.g. about 1, 5, 10, 15, 20, 25, 30, 35, 40, 45, 50, 55, 60, 65, 70, 75, 80, 85, 90, 95, or 100 mmol) or more, e.g. hundreds or thousands of mmols in industrial preparations; and the grams of carbon nanotubes can vary from about e.g. 0.1 to about 10 g (e.g. about 1, 2, 3, 4, 5, 6, 7, 8, 9, or 10 g, including all decimal fractions in between) or more, e.g. tens, hundreds or thousands of grams in industrial preparations. Generally, from about 2-50 fold excess of grams of carbon nanotubes to mmoles of Pd(II) is utilized, e.g. about 2, 5, 10, 15, 20, 25, 30, 35, 40, 45 or 50 fold. The diameter and exact type of the milling balls may vary (e.g. the diameter may vary from about 5 to about 25, and other types such as steel, ceramic, lead, etc. may be used). Further, the distance of back and forth shaking may vary e.g. from about 2 cm to about 10 cm and the distance of side-to-side shaking may vary e.g. from about 0.5 cm to about 5 cm. The milling may be carried out at e.g. about 500 to 2000 cycles/minute at room temperature, +/−about 10° C. Similarly, the time of milling can vary, e.g. from about 1 to about 15 minutes, e.g. about 1, 2, 3, 4, 5, 6, 7, 8, 9, 10, 11, 12, 13, 14, or 15 mins). However, in order to obtain solid-supported catalysts containing predominantly palladium (II), milling times under 15 minutes are required. Longer milling times (over 15 minutes) give solid-supported catalysts composed of predominantly Pd(0).

Methods of making a compound of interest, M-C—X, are also provided. The methods involve contacting a substrate compound or molecule (M) with a solid-supported solid-supported Pd(II) catalyst, e.g. a Pd(II)/MWCNT catalyst. The substrate molecule M comprises at least one C—H group capable of chelating Pd(II) and at least one additional or second atom that is part of a directing group and which also chelates Pd(II). Chelation occurs in a manner that allows the Pd(II)/MWCNT catalyst to displace H from C—H and coordinate with the C and the second atom, thereby forming a Pd(II) chelation adduct (M-Pd(II)). Reacting, under oxidizing conditions, the M-Pd(II) adduct with an oxidant which comprises at least one atom of X e.g. oxidant Z—X, results in formation of a second chelation adduct, M-Pd(IV)-X, X having been removed from oxidant Z—X, and Pd)II) having been converted to Pd(IV). Thereafter, under reducing conditions, the M-Pd(IV)-X adduct undergoes reductive elimination, releasing the product M-C—X and regenerated Pd(II) catalyst.

A more generalized description of the process is as follows: The substrate, compound or molecule (M) is mixed with the solid-supported Pd(II) catalyst and an oxidant in a compatible solvent and the mixture is heated to the appropriate temperature until the reaction is complete. The nature of the oxidant defines the FG (X) that is installed in the substrate compound or molecule (M) as well as the solvent and temperature that are required. Once the reaction is complete, the solid-supported catalyst is removed by filtration and very little Pd metal is left behind (<250 ppb). The byproduct (the reduced form of the oxidant) can be removed by any of several methods including acid-base washing and/or column chromatography. Following these steps, the purified, selectively functionalized compound of interest (M-C—X) of the reaction can be isolated by evaporation.

The reaction conditions for each of the C—H activation transformations are summarized in Table 1. For all the C—H activation transformations, the amount of the substrate is generally in the range of from about 0.01 to about 100 mmol and the loading of the solid-supported Pd(II) catalyst is generally in the range of from about 0.5 to 20 mol % relative to the amount of substrate. The amount of the oxidant compound that bears the X or FG group is generally in the range of from about 1 to about 3 equivalents (relative to the amount of substrate) for the C—H to C—O, C-halogen, C—C, and C—F transformations and generally in the range of from about 1 to about 5 equivalents (relative to the amount of substrate) for the C—H to C—N and C—CF$_3$ transformations.

Solvents useful for performing the C—H activation reactions described herein include but are not limited to polar and non-polar, protic and aprotic solvents as indicated in Table 1 depending on the specific transformation. These solvents include but are not limited to AcOH, MeOH, other alkyl, alkenyl, or aryl alcohols (such as EtOH, vinyl alcohol, or phenol), acetonitrile (MeCN), toluene, 1,2-dichloroethane (DCE), and trifluorobenzene (CF$_3$Ph). The concentration of the substrate in the reaction solvent is generally in the range of from about 0.05 to about 2 M. The reactions are generally carried out within a temperature range of from about 0 to about 120° C. for a period of time ranging from about 10 minutes (0.2 hours) to about 24 hours, depending on the specific transformations.

A plethora of molecules can be produced using the reactions described herein. For example, the use of the N-heterocyclic aryl motif that can act as a directing group in this chemistry is ubiquitous in small molecule drugs. ~25% of the Top 200 Drugs (by retail sales) contain this motif and in particular it is found in all of the 25 FDA-approved kinase inhibitors. Therefore, chemical technologies such as the present technology, which can selectively and directly functionalize this motif, are in high demand in pharmaceutical industry-related markets.

Specifically, the chelation-directed C—H activation methodology is useful, for example, for the synthesis of analogues of new and/or known kinase inhibitors for the treatment of cancer and other diseases. Most known kinase inhibitors, including the FDA-approved kinase inhibitors imatinib, nilotinib, gefetinib, and erlotinib, contain an N-heterocyclic aryl motif that could be used as the directing group for the present methodology. The direct C—H functionalization of these scaffolds can be used as either a key step in the manufacturing process or as a methodology to synthesize analogues while performing structure-activity relationship studies for the development of new kinase inhibitors.

Those of skill in the art will recognize that the catalyst preparation methods disclosed herein can be readily converted to industrial scale since ball milling is routinely carried out in large commercial operations. The solid-supported nature of the catalyst allows for these materials to be used in, for example, plug-flow reactor systems with packed beds of catalyst that can be readily scaled to commercial continuous operations. This is reinforced by the fact that very low residual palladium concentrations (<250 ppb) have been observed when using the present catalysts and can be recycled multiple times, which allows for a large cost-savings for industrial-scale reactions. The use of these catalysts in continuous operations offers a substantial advantage for scale up because the production output is controlled to a large extent by the amount of time that the process is run, not the batch size that is used.

TABLE 1

Reaction Conditions for C—H Activation Reactions.

| Reaction Condition | C—H Activation Reactions. Conversion of C—H to: | | | | | |
|---|---|---|---|---|---|---|
| | C—O | C—Cl/Br/I | C—C | C—N | C—F | C—CF$_3$ |
| Substrate Scale | 0.01-100 mmol | 0.01-100 mmol | 0.01-100 mmol | 0.01-100 mmol | 0.01-100 mmol | 0.01-100 mmol |
| Oxidant (equivalents) | 1-3 eq. | 1-3 eq. | 1-3 eq. | 1-5 eq. | 1-3 eq. | 1-5 eq. |
| Catalyst Loading | 0.5-20 mol % | 0.5-20 mol % | 0.5-20 mol % | 0.5-20 mol % | 0.5-20 mol % | 0.5-20 mol % |
| Solvent(s) | Polar protic; i.e. AcOH, MeOH, ROH | Polar protic or aprotic; i.e. AcOH, MeCN | Polar protic or aprotic; i.e. AcOH, toluene | Polar aprotic; i.e. DCE | Non-polar or polar aprotic; i.e. benzene, MeCN in CF$_3$Ph | Polar aprotic; i.e. DCE |
| Reaction Concentration | 0.05-2.0M | 0.05-2.0M | 0.05-2.0M | 0.05-2.0M | 0.05-2.0M | 0.05-2.0M |
| Temperature | 0-120° C. | 0-120° C. | 0-120° C. | 0-120° C. | 0-120° C. | 0-120° C. |
| Time | 0.2-8 h | 0.2-8 h | 0.2-18 h | 0.2-24 h | 0.2-18 h | 0.2-24 h |

Examples

Example 1. Selective N-Chelation-Directed C—H Activation Reactions Catalyzed by Solid-Supported Pd(II) on Multi-Walled Carbon Nanotubes (MWCNT): C—H to C—O Transformations Chelation-directed C—H activation reactions that utilize the Pd(II)/Pd(IV) catalytic cycle have been reported. However, to date, these reactions have only been reported using homogenous palladium catalysts. Here we report the first use of a solid-supported Pd(II) catalyst [Pd(II) on multi-walled carbon nanotubes, Pd(II)/MWCNT] to carry out chelation-directed transformations. Coupling reactions using these solid-supported nanoparticle catalysts display remarkable catalytic activity with high turnover number (TON) and turnover frequency (TOF). The reactions generally are complete within 10 minutes, can optionally be run at lower temperature (~80° C.) using either conventional or microwave heating, and can be run in either batch or flow format. The results presented in this Example demonstrate that solid-supported Pd(II)/MWCNT catalysts effectively catalyze oxidative C—H to C—OMe/OAc, C—Cl and C—Br functionalizations.

In this example, we demonstrate that a solid-supported nanoparticle catalyst containing predominantly Pd(II) on multi-walled carbon nanotubes (Pd(II)/MWCNT) can be used to catalyze oxidative N-chelation-directed C—H activation reactions that undergo the Pd(II)/Pd(IV) catalytic cycle. We demonstrated the ability of this catalyst to carry out oxidative C—H to C—OMe/OAc, C—Cl, and C—Br functionalizations.

To begin our work, we chose substrates from the literature that have been previously reported to undergo C—H functionalization reactions, so that we could compare the results of the solid-supported Pd(II)/MWCNT catalyst to that of the known homogenous Pd(II) system (Pd(OAc)$_2$). We first explored the C—H to C—O transformation, which utilizes PhI(OAc)$_2$ as the oxidant (Table 2). Treatment of 8-methylquinoline with Pd(II)/MWCNT and PhI(OAc)$_2$ in acetic acid at 120° C. for 10 minutes (Table 2, entry 1) afforded the desired 8-(acetoxymethyl)quinoline in 90% yield, comparable to the previously reported yield of 88% with a homogeneous catalyst.[1a] However, treatment of benzo[h]quinoline (entry 2) and 2-phenylpyridine (entry 3) failed to give any of the desired acylation products, even at extended reaction times and higher temperatures. Only starting material was recovered in these reactions.

TABLE 2

C—H to C—O Functionalizations Catalyzed by Pd(II)/MWCNT

Pd(II)/MWCNT (5 mol %), PhI(OAc)$_2$ (2 eq), AcOH or MeOH

| Entry[a] | Product | Solid-supported Pd(II)/MWCNT Temp | Time | Yield | Yield and time with Pd(OAc)$_2$[b] |
|---|---|---|---|---|---|
| 1 | 8-(acetoxymethyl)quinoline (AcO) | 120° C. | 0.2 h | 90% | 88%, 22 h |
| 2 | benzo[h]quinoline-AcO | 120° C. | 1 h | 0% | 86%, 12 h |
| 3 | 2-phenylpyridine-AcO | 120° C. | 1 h | 0% | 52%, 12 h |
| 4 | 8-(methoxymethyl)quinoline (MeO) | 100° C. | 0.2 h | 99% | 77%, 18 h |

TABLE 2-continued

C—H to C—O Functionalizations Catalyzed by Pd(II)/MWCNT

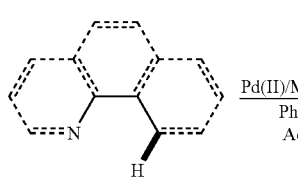

| Entry[a] | Product | Solid-supported Pd(II)/MWCNT | | | Yield and time with Pd(OAc)$_2$[b] |
|---|---|---|---|---|---|
| | | Temp | Time | Yield | |
| 5 | (structure with MeO) | 100° C. | 0.2 h | 90% | 95%, 22 h |
| 6 | (structure with MeO) | 100° C. | 5 h | 25% | —[c] |

[a]Solvent for entries 1-3: AcOH; entries 4-6: MeOH.
[b]Previous reported results with homogeneous Pd(OAc)$_2$; see Ref 1a.
[c]Yield with homogeneous Pd catalyst has not been reported.

Having confirmed that solid-supported Pd(II)/MWCNT can catalyze a reaction that undergoes the Pd(II)/Pd(IV) catalytic cycle and encouraged by the initial success of the acylation reaction with 8-methylquinoline, we explored whether other oxygen containing functional groups could be installed using the catalyst. To test this, we repeated the reaction of 8-methylquinoline with Pd(H)/MWCNT and PhI(OAc)$_2$, except this time using methanol as a solvent (Table 2, entry 4). Gratifyingly, we obtained a near quantitative yield (99%) of the desired 8-(methoxymethyl)quinoline in 10 minutes at 100° C., better than the reported yield of 77% with the homogeneous catalyst system. Application of these conditions to benzo[h]quinoline (entry 5) afforded a 90% yield, again comparable to the reported yield with the homogeneous catalyst (95%). Finally, treatment of 2-phenylpyridine with Pd(II)/MWCNT/PhI(OAc)$_2$/MeOH (entry 3) did result in formation of the product after extended reaction time, albeit in much lower yield (25%).

We next sought to explore whether alcohols other than methanol could be installed in substrates using the solid-supported catalyst. To test this, we repeated the reaction of benzo[h]quinolone with Pd(II)/MWCNT and PhI(OAc)$^2$ in alcohol solvents (Table 3), which demonstrated that methoxy (from methanol, entry 1, product 5) and ethoxy (from ethanol, entry 2, product 7) functional groups could be installed in moderate to high yields with the catalyst. However, as the size of the alcohol increased, incorporation of the functional group into the product decreased (with isopropyl, entry 3, product 8) and eventually failed (in the tert-butyl case, entry 4, product 9).

TABLE 3

C—H to C—O-Alkyl Functionalizations Catalyzed by Pd(II)/MWCNT

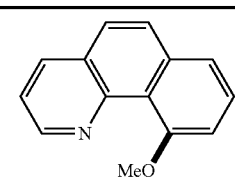

| | | | Yield | |
|---|---|---|---|---|
| Entry | ROH | Product | Pd(II)/MWCNT | Pd(OAc)$_2$ |
| 1 | MeOH | (structure with MeO) | 90% | 95% |

TABLE 3-continued

C—H to C—O-Alkyl Functionalizations Catalyzed by Pd(II)/MWCNT

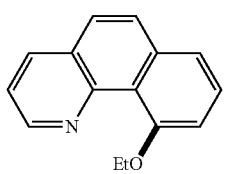

| | | | Yield | |
|---|---|---|---|---|
| Entry | ROH | Product | Pd(II)/MWCNT | Pd(OAc)$_2$ |
| 2 | EtOH | (benzo[h]quinoline-OEt) | 73% | 80% |
| 3 | iPrOH | (benzo[h]quinoline-OiPr) | 33% | 72% |
| 4 | tBuOH | (benzo[h]quinoline-OtBu) | 0% | —[a] |

[a]Yield with homogeneous Pd catalyst has not been reported.

Figure 8:
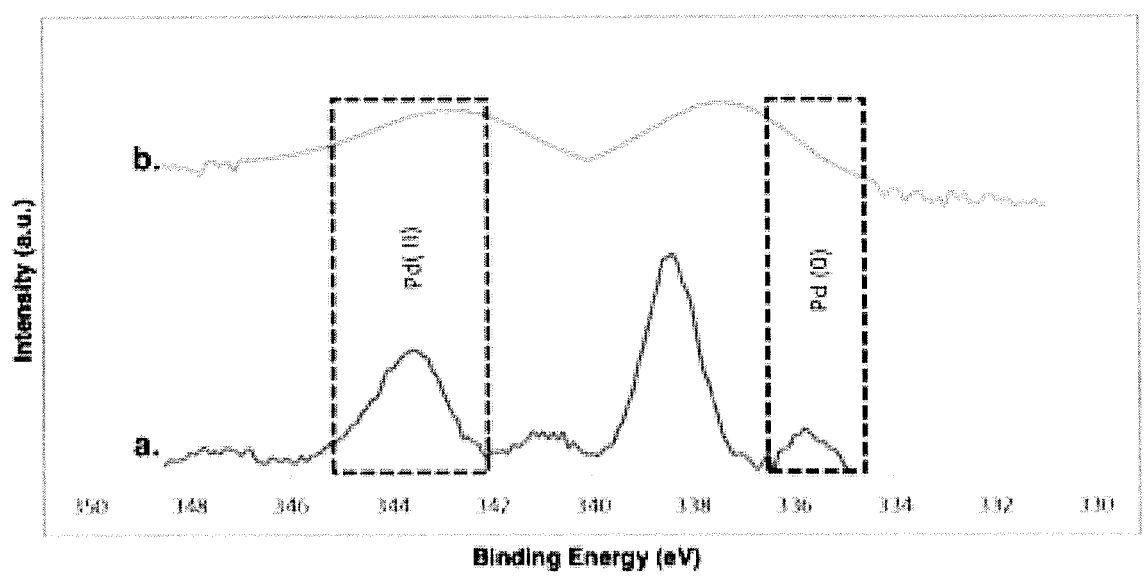
FIG. 8. Pd(II) and Pd(0) content in Pd(II)/MWCNT before (a.) and after (b.) a C—H Activation Reaction as measured by XPS.

To characterize the solid-supported Pd(II)/MWCNT catalyst, we measured the composition of the palladium both before and after C—H activation reaction by XPS (FIG. 8). Prior to use in the C—H activation reactions, the solid-supported catalyst was found to be a mixture of Pd(II) (76.54%) and Pd(0) (23.46%), with Pd(II) being the predominant component (FIG. 8, line a). After the C—H to C—OMe functionalization of benzo[h]quinoline (Table 2, entry 5), XPS showed that the solid-supported catalyst contained only Pd(II) (100%, FIG. 8, line b). This data shows that all of the Pd(0) in the catalyst prior to the reaction is converted to Pd(II) and supports the mechanism that these reactions use Pd(II) as the starting oxidation state.

One of the major advantages of solid-supported catalysts is that the active catalytic species is not dissolved in the reaction mixture and that the products are not contaminated with potentially toxic residual metal. To determine whether the palladium metal from the solid-supported Pd(II)/MWCNT catalyst leeched into the C—H activation reactions and contaminated the products, we removed the catalyst by filtration over Celite® from a C—H to C—OMe functionalization reaction on benzo[h]quinoline (Table 2, entry 5) and measured the palladium content in solution by ICP-MS. The palladium content of the reaction mixture was found to be <250 ppb, demonstrating that very little metal leeched into the reaction medium. Combined with the ease of removing catalyst from the reactions mixtures, this low level of contamination by potentially toxic palladium is an improvement on the existing N-chelation-directed C—H activation method.

To demonstrate that the trace Pd in the reaction mixture is not the source of catalytic activity, a hot filtration experiment was performed with benzo[h]quinoline(Table 2, entry 5). After 10 min. at 100° C., the Pd(II).MWCNT catalyst was removed by hot filtration over Celite®. Fresh substrate and oxidant were added to the filtrate, which was reheated to 100° C. No further conversion to product or catalytic activity was observed in the filtrate in the absence of Pd(II).MW-CNT, showing that the <250 ppb of residual Pd that remained in solution was not adequate to catalyze the C—H activation reaction.

To demonstrate the ability of the Pd(II)/MWCNT catalyst to be recycled, we ran the C—H to C—OMe functionalization on 8-methylquinoline (Table 2, entry 4), recovered the catalyst by centrifugation, and iteratively repeated the reaction with the same batch of catalyst. We were able to recycle the catalyst a remarkable 16 times with minimal reduction in yield and no catalyst deactivation (Table 4). We terminated the experiment after 16 cycles and have yet to determine the limits of the recyclability of the catalyst. Images of the catalyst before (FIG. 9A) and after (FIG. 9B) the first reaction by TEM show that the overall structure of the catalyst is not changed by the C—H activation reaction.

TABLE 4

Recycling experiments with Pd(II)/MSCNT

| Run | Conversion (%)[a] |
|---|---|
| 1 | 98 |
| 2 | 98 |
| 3 | 92 |
| 4 | 90 |
| 5 | 90 |
| 6 | 90 |
| 7 | 90 |
| 8 | 90 |
| 9 | 89 |
| 10 | 90 |
| 11 | 90 |
| 12 | 90 |
| 13 | 90 |
| 14 | 90 |
| 15 | 90 |
| 16 | 90 |
| 17 | 90 |

[a]Conversion was determined by GC/MS based upon the consumption of the starting material.

For the C—H to C—O transformations, we observed that the reactions catalyzed by Pd(II)/MWCNT seemed to be faster than those with the homogeneous Pd(OAc)$_2$. To quantify this, we calculated turnover frequencies (TOF) for one example reaction for each functionalization (Table 5) for both the solid-supported Pd(II)/MWCNT and homogeneous palladium catalysts. For the C—H to C—OAc and C—OMe functionalization reactions, the turnover frequencies for the solid-supported Pd(II)/MWCNT catalyst were ~27-fold higher than for the homogeneous catalyst. This represents a significant improvement over previously reported results, particularly with regards to the C—H to C—OMe functionalization reactions.

TABLE 5

Comparison of Turnover Frequencies in C—H to C—OAc and C—OMe Reactions Catalyzed by Solid-supported Pd(II)/MWCNT and Homogeneous Pd(OAc)$_2$

| Entry | Product | Turnover Frequency (h$^{-1}$)[a] | | Fold increase |
|---|---|---|---|---|
| | | Pd(II)/MWCNT | Pd(OAc)$_2$ | |
| 1 | (quinoline-CH$_2$-OAc) | 106.44 | 4.02 | 26.48 |
| 2 | (benzo[h]quinoline-OMe) | 106.94 | 3.79 | 28.22 |

[a]Calculated as mol product/mol palladium/h.

In conclusion, we have demonstrated that solid-supported Pd(II)/MWCNT can catalyze N-chelation-directed C—H to C—OAc and C—OMe activation reactions. For the C—H to C—O functionalizations, steric crowding around the reactive palladium center in the solid-supported catalyst led to decreased yields as the size of the functional group being installed increased. The solid-supported catalyst has a higher turnover frequency than the reported homogenous catalyst and offers the advantages of ease of removal by filtration and low levels of residual palladium metal contamination in the products.

Example 2. Selective N-Chelation-Directed C—H Activation Reactions Catalyzed by Solid-Supported Pd(II) on Multi-Walled Carbon Nanotubes (MWCNT): C—H to C—Cl and C—Br Transformations Having demonstrated that solid-supported Pd(II)/MWCNT can catalyze the C—H to C—O functionalization reaction, we next turned our attention to halogenation reactions (Table 6). Treatment of benzo[h]quinoline with Pd(II)/MWCNT and N-chlorosuccinimide (NCS) in acetonitrile at 100° C. for 5 hours (Table 6, entry 1) afforded the desired 10-chlorobenzo[h]quinoline (10) in 92% yield, comparable to the previously reported yield of 95% with the homogeneous catalyst. It should be noted that the reaction with the Pd(II)/MWCNT is much faster than with homogeneous Pd(OAc)$_2$ (5 h vs. 3 days). Chlorination of (E)-3,4-dihydronaphthalen-1(2H)-one O-methyl oxime (entry 2), 2-phenylpyridine (entry 3), and 3-methyl-2-phenylpyridine (entry 4) in either acetic acid (entries 2 and 4) or acetonitrile (entry 3) all afforded the desired chlorinated products 11-13 in moderate yields in reaction times from 10 minutes to 6 hours. While the yields for these transformations are lower than the comparable reaction with homogeneous catalyst, the reaction times are much shorter, pointing to faster reaction kinetics (vida infra). The 2-phenylpyridine substrates (entries 3 and 4) required additional catalyst to reach this level of conversion and product isolation. For all of these substrates, further increasing the number of equivalents of NCS led to the formation of other products.

TABLE 6

C—H to C—Cl/C—Br Functionalizations Catalyzed by Pd(II)/MWCNT

Pd(II)/MWCNT (5 mol %), NBS or NCS (1.2 eq), MeCN or AcOH

R = Cl or Br

| entry[a,b] | Product | Solid-supported Pd(II)/MWCNT | | | Pd(OAc)$_2$ |
| --- | --- | --- | --- | --- | --- |
| | | Temp | Time | Yield | Yield and time |
| 1 | | 100° C. | 5 h | 92% | 95%, 3 days |
| 2 | | 120° C. | 1.5 h | 61% | 88%, 12 h |
| 3 | | 100° C. | 6 h | 55%[c] | —[e] |
| 4 | | 120° C. | 0.2 h | 50%[c] | 65%, 12 h |
| 5 | | 100° C. | 1.5 h | 89%[d] | 93%, 1.5 days |
| 6 | | 120° C. | 5 h | 30% | 62%, 12 h |
| 7 | | 100° C. | 6 h | 40%[d] | 63%, 12 h |

TABLE 6-continued

C—H to C—Cl/C—Br Functionalizations Catalyzed by Pd(II)/MWCNT

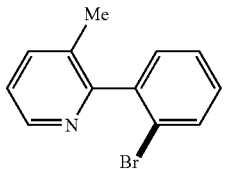

R = Cl or Br

| | | Solid-supported Pd(II)/MWCNT | | | Pd(OAc)$_2$ |
|---|---|---|---|---|---|
| entry[a,b] | Product | Temp | Time | Yield | Yield and time |
| 8 | Me-pyridine-phenyl-Br | 120° C. | 5 h | 51% | 56%, 12 h |

[a]Oxidants for entries 1-4: NCS; entries 5-8: NBS.
[b]Solvents for entries 1, 3, 5, and 7: MeCN; entries 2, 4, 6, and 8: AcOH.
[c]10 mol % Pd(II)/MWCNT was used.
[d]1.5 eq of NBS was used.
[e]A directly analogous yield for the homogeneous catalyst has not been reported.

Turning to the C—H to C—Br functionalizations, treatment of benzo[h]quinoline with Pd(II)/MWCNT and N-bromosuccinimide (NBS) in acetonitrile at 100° C. for 1.5 hours (Table 6, entry 5) afforded the desired 10-bromobenzo[h]quinoline in 89% yield, comparable to the previously reported yield of 93% with the homogeneous catalyst. Again, it should be noted that the reaction with the Pd(II)/MWCNT is much faster than with homogeneous Pd(OAc)$_2$ (1.5 h vs. 1.5 days). Bromination of (E)-3,4-dihydronaphthalen-1(2H)-one O-methyl oxime (entry 6), 2-phenylpyridine (entry 7), and 3-methyl-2-phenylpyridine (entry 8) in either acetic acid (entries 6 and 8) or acetonitrile (entry 7) all afforded the desired brominated products 15-17 in moderate yields in reaction times of 5-6 hours. Again, the yields are lower than the comparable reaction with homogeneous catalyst but the reaction times are much shorter, pointing to faster reaction kinetics (vida infra). Both the benzo[h]quinoline and 2-phenylpyridine substrates (entries 5 and 7) required additional NBS (1.5 eq vs. 1.2 eq) to reach this level of conversion and product isolation. Increasing the number of equivalents of NBS beyond 1.5 eq led to the formation of other products. For the brominations, increasing the catalyst loading did not further increase conversion or isolated yield.

For all of the C—H activation reactions, we observed that the reactions catalyzed by Pd(II)/MWCNT seemed to be faster than those with the homogeneous Pd(OAc)$_2$. To quantify this, we calculated turnover frequencies (TOF) for one example reaction for each functionalization (Table 7) for both the solid-supported Pd(II)/MWCNT and homogeneous palladium catalysts. For the C—H to C—Cl and C—Br reactions, the turnover frequencies for the solid-supported Pd(II)/MWCNT catalyst were ~4-fold higher.

TABLE 7

Comparison of Turnover Frequencies in C—H to C—Cl and C—Br Reactions Catalyzed by Solid-supported Pd(II)/MWCNT and Homogeneous Pd(OAc)$_2$

| | | Turnover Frequency (h$^{-1}$)[a] | | |
|---|---|---|---|---|
| Entry | Product | Pd(II)/MWCNT | Pd(OAc)$_2$ | Fold increase |
| 1 | 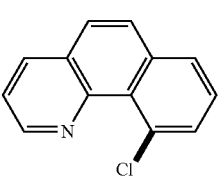 | 3.60 | 0.73 | 4.90 |

TABLE 7-continued

Comparison of Turnover Frequencies in C—H to C—Cl and C—Br Reactions Catalyzed by Solid-supported Pd(II)/MWCNT and Homogeneous Pd(OAc)₂

| | | Turnover Frequency (h⁻¹)[a] | | |
|---|---|---|---|---|
| Entry | Product | Pd(II)/MWCNT | Pd(OAc)₂ | Fold increase |
| 2 | 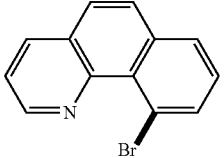 | 9.96 | 2.63 | 3.75 |

[a]Calculated as mol product/mol palladium/h.

In conclusion, we have also demonstrated that solid-supported Pd(II)/MWCNT can catalyze N-chelation-directed C—H to C—Cl and C—Br activation reactions. For all of the C—H activation reaction examined, the solid-supported catalyst has a higher turnover frequency than the reported homogenous catalyst. The solid-supported Pd(II)/MWCNT also offers the advantages of ease of removal by filtration and low levels of residual palladium metal contamination in the products. This catalyst can be utilized in other N-chelation-directed C—H activation reactions.

REFERENCES FOR EXAMPLES 1 AND 2

(1) (a) Dick, A. R.; Hull, K. L.; Sanford, M. S., J. Am. Chem. Soc. 2004, 126, 2300-2301; (b) Desai, L. V.; Hull, K. L.; Sanford, M. S., J. Am. Chem. Soc. 2004, 126, 9542-9543.
(2) (a) Kalyani, D.; Dick, A. R.; Anani, W. Q.; Sanford, M. S., Org. Lett. 2006, 8, 2523-2526; (b) Kalyani, D.; Dick, A. R.; Anani, W. Q.; Sanford, M. S., Tetrahedron 2006, 62, 11483-11498.
(3) (a) Kalyani, D.; Deprez, N. R.; Desai, L. V.; Sanford, M. S., J. Am. Chem. Soc. 2005, 127, 7330-7331; (b) Deprez, N. R.; Sanford, M. S., J. Am. Chem. Soc. 2009, 131, 11234-11241.
(4) (a) Thu, H.-Y.; Yu, W.-Y.; Che, C.-M., J. Am. Chem. Soc. 2006, 128, 9048-9049; (b) Dick, A. R.; Remy, M. S.; Kampf, J. W.; Sanford, M. S., Organometallics 2007, 26, 1365-1370.
(5) (a) Hull, K. L.; Anani, W. Q.; Sanford, M. S., J. Am. Chem. Soc. 2006, 128, 7134-7135; (b) McMurtrey, K. B.; Racowski, J. M.; Sanford, M. S., Org. Lett. 2012, 14, 4094-4097.
(6) Ye, Y.; Ball, N. D.; Kampf, J. W.; Sanford, M. S., J. Am. Chem. Soc. 2010, 132, 14682-14687.
(7) (a) Dick, A. R.; Kampf, J. W.; Sanford, M. S., J. Am. Chem. Soc. 2005, 127, 12790-12791; (b) Whitfield, S. R.; Sanford, M. S., J. Am. Chem. Soc. 2007, 129, 15142-15143.
(8) Djakovitch, L.; Felpin, F.-X., ChemCatChem 2014, 6, 2175-2187.
(9) Siamaki, A. R.; Lin, Y.; Woodberry, K.; Connell, J. W.; Gupton, B. F., J. Mater. Chem. A 2013, 1, 12909-12918.

Reactions for Examples 1 and 2

All the reactions were carried out in vials sealed with Teflon lined caps under ambient atmosphere. Benzo[h]quinoline and 3-methyl-2-phenylpyridine were purchased from TCI, 2-phenylpyridine was purchased from Chem-Impex. All solvents were purchased from VWR and other chemicals were purchased from Sigma-Aldrich and all were used without distillation or purification. Analytical Thin Layer Chromatography (TLC) was performed using silica gel GHLF plates (Analtech Inc., DE, USA). Flash chromatography was performed on TELEDYNE ISCO CombiFlash® Rf instrument using RediSep Rf Normal-phase Flash Columns (4-gm, 12-gm, 24-gm or 40-gm). NMR spectra were recorded on Bruker 400 MHz instrument operating at 400 MHz for ¹H and 125 MHz for ¹³C acquisitions. Electrospray ionization (ESI) mass spectra were obtained from Perkin Elmer Flexar UPLC/AxION2 TOF Mass Spectrometer. The X-ray photoelectron spectroscopy (XPS) analysis was performed on a Thermo Fisher Scientific ESCALAB 250 using a monochromatic Al KR X-ray. The Pd content in the Pd nanoparticles supported on carbon nanotubes before and after reaction was determined using an Inductively Coupled Plasma equipped with Mass Spectrometry (ICP-MS, Varian 820-MS).

Synthesis of Pd(II) Nanoparticles on Multi-Walled Carbon Nanotubes by Ball Milling Palladium (II) acetate (0.013 g, 4.6 mmol) and multi-walled carbon nanotubes (0.500 g) were loaded in a 45 ml zirconia grinding vial. Two 12.77 mm diameter zirconia balls were also placed in the vial before sealing. The container was then placed in an 8000 M Spex Miser/Mill. The contents in the mixer were shaken back and forth 5.9 cm and side-to-side 2.5 cm for 10 min at room temperature at 115 volts (1060 cycles/min). The resulting solid was collected and used directly in reactions. The shorter ball-milling time of 10 minutes results in a Pd(II)/Pd(0) ratio of 76.54% to 23.46%.

Procedure for Recycling Experiment

To a solution of 8-methylquinoline (20 mg, 0.14 mmol) in methanol (1.2 mL) in a 10 mL reaction vial, was added Ph(OAc)₂ (89 mg, 0.28 mmol) and Pd(II)/MWCNT (7 mg, 5 mol %). The vial was sealed and the reaction mixture was heated to 100° C. for 10 min. Upon the completion of the reaction period, the mixture was diluted with 2 mL methanol and shaken. The entire mixture was centrifuged and the solvent abvet the Pd/MWCNT nanoparticles was then reused for the subsequence reaction using fresh reagents (8-methodquinoline, PhI(OAc)₂, and methanol. This procedure was applied for every recycling experiment and the percent conversion to the products was determined by means of GS-MS spectroscopy.

Procedure for Hot Filtration Experiment

Benzo[h]quinolone (25 mg, 0.14 mmol) in methanol (1.2 mL) was heated in the presence of Pd(II)/MWCNT (7 mg, 5 mol %) and PhI(OAc)₂ (89 mg, 0.28 mmol) in a 10 mL reaction vial at 100° C. for 10 min, resulting in 95% conversion to the product according to the GC-MS analysis. The reaction mixture was then hot filtered over Celite® and the filtrate solution was subjected to Inductively coupled plasma mass spectrometry (ICP-MS) in which the amount of Pd content was determined to be <250 ppb. Fresh reagents (Benzo[h]quinolone (25 mg, 0.14 mmol) and PhI(OAc)$_2$ (89 mg, 0.28 mmol) were added to the filtrate solution, and the mixture was heated at 100° C. for 10 min. No further catalytic activity was observed in this mixture, as measured by GC/MS.

Quinolin-8-ylmethyl acetate (1)[1]

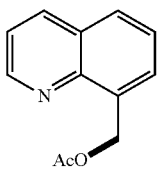

1

PhI(OAc)$_2$ (89 mg, 0.28 mmol) and Pd-MWCNT (7 mg, 5 mol %) were added to a solution of 8-methylquinoline (20 mg, 0.14 mmol) in AcOH (1.2 ml). The reaction was heated at 120° C. for 10 min. After cooling to room temperature, it was diluted with EtOAc and washed with brine. The organic layer was filtered through Celite®, Na$_2$SO$_4$ and dried. The crude product was purified by flash chromatography (silica gel, 20% EtOAc/n-hexane) to give the product as a white solid (25 mg) in 90% yield. Analytical data ($^1$H NMR, $^{13}$C NMR, mass spec) matched the previously reported data.[1]

8-(Methoxymethyl)quinolone (4)[1]

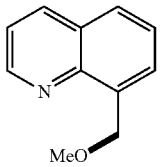

4

PhI(OAc)$_2$ (89 mg, 0.28 mmol) and Pd-MWCNT (7 mg, 5 mol %) were added to a solution of 8-methylquinoline (20 mg, 0.14 mmol) in methanol (1.2 ml). The reaction was heated at 100° C. for 10 min. After cooling to room temperature, it was diluted with EtOAc, filtered through Celite®, Na$_2$SO$_4$ and dried. The crude product was purified by flash chromatography (silica gel, 20% EtOAc/n-hexane) to give the product as yellow oil (24 mg) in 99% yield. Analytical data ($^1$H NMR, $^{13}$C NMR, mass spec) matched the previously reported data.[1]

10-Methoxybenzo[h]quinolone (5)[1]

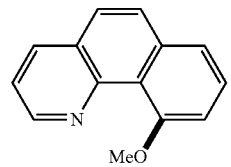

5

PhI(OAc)$_2$ (89 mg, 0.28 mmol) and Pd-MWCNT (7 mg, 5 mol %) were added to a solution of benzo[h]quinoline (25 mg, 0.14 mmol) in methanol (1.2 ml). The reaction was heated at 100° C. for 10 min. After cooling to room temperature, it was diluted with EtOAc, filtered through Celite®, Na$_2$SO$_4$ and dried. The crude product was purified by flash chromatography (silica gel, 5% MeOH/DCM) to give the product as a pale yellow solid (26 mg) in 90% yield. Analytical data ($^1$H NMR, $^{13}$C NMR, mass spec) matched the previously reported data.[1]

2-(2-Methoxyphenyl)pyridine (6)[2]

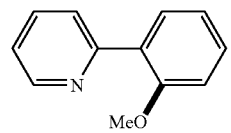

6

PhI(OAc)$_2$ (87 mg, 0.27 mmol) and Pd-MWCNT (10 mg, 5 mol %) were added to a solution of 2-phenylpyridine (30 mg, 0.19 mmol) in methanol (1.6 ml). The reaction was heated at 100° C. for 5 h. After cooling to room temperature, it was diluted with EtOAc, filtered through Celite®, Na$_2$SO$_4$ and dried. The crude product was purified by flash chromatography (silica gel, 20% EtOAc/n-hexane) to give the product as a clear liquid (9 mg) in 25% yield. Analytical data ($^1$H NMR, $^{13}$C NMR, mass spec) matched the previously reported data.[2]

10-Ethoxybenzo[h]quinolone (7)[1]

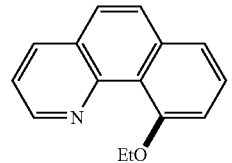

7

PhI(OAc)$_2$ (89 mg, 0.28 mmol) and Pd-MWCNT (7 mg, 5 mol %) were added to a solution of benzo[h]quinoline (25 mg, 0.14 mmol) in ethanol (1.2 ml). The reaction was heated at 100° C. for 10 min. After cooling to room temperature, it was diluted with EtOAc, filtered through Celite®, Na$_2$SO$_4$ and dried. The crude product was purified by flash chromatography (silica gel, 5% MeOH/DCM) to give the product as thick oil (22.6 mg) in 73% yield. Analytical data ($^1$H NMR, $^{13}$C NMR, mass spec) matched the previously reported data.[1]

10-Isopropoxybenzo[h]quinolone (8)'

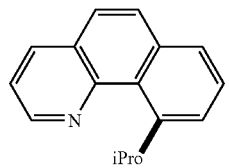

PhI(OAc)$_2$ (89 mg, 0.28 mmol) and Pd-MWCNT (7 mg, 5 mol %) were added to a solution of benzo[h]quinoline (25 mg, 0.14 mmol) in isopropanol (1.2 ml). The reaction was heated at 100° C. for 3 h. After cooling to room temperature, it was diluted with EtOAc, filtered through Celite®, Na$_2$SO$_4$ and dried. The crude product was purified by flash chromatography (silica gel, 5% MeOH/DCM) to give the product as brown oil (11 mg) in 33% yield. Analytical data ($^1$H NMR, $^{13}$C NMR, mass spec) matched the previously reported data.[1]

10-Chlorobenzo[h]quinolone (10)[1]

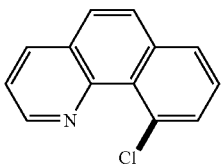

NCS (21 mg, 0.16 mmol) and Pd-MWCNT (7 mg, 5 mol %) were added to a solution of benzo[h]quinoline (25 mg, 0.14 mmol) in ACN (1.2 ml). The reaction was heated at 100° C. for 5 h. After cooling to room temperature, it was diluted with EtOAc, filtered through Celite®, Na$_2$SO$_4$ and dried. The crude product was purified by flash chromatography (silica gel, 10% EtOAc/n-hexane) to give the product as a white solid (27 mg) in 92% yield. Analytical data ($^1$H NMR, $^{13}$C NMR, mass spec) matched the previously reported data.[1]

(E)-8-Chloro-3,4-dihydronaphthalen-1(2H)-one O-methyl oxime (11)[3]

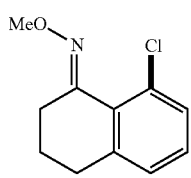

NCS (24 mg, 0.18 mmol) and Pd-MWCNT (9 mg, 5 mol %) were added to a solution of (E)-3,4-dihydronaphthalen-1(2H)-one O-methyl oxime (30 mg, 0.17 mmol) in AcOH (1.4 ml). The reaction was heated at 120° C. for 1.5 h. After cooling to room temperature, it was diluted with EtOAc, washed with brine. The organic layer was filtered through Celite®, Na$_2$SO$_4$ and dried. The crude product was purified by flash chromatography (silica gel, 5% EtOAc/n-hexane) to give the product as clear oil (22 mg) in 61% yield. Analytical data ($^1$H NMR, $^{13}$C NMR, mass spec) matched the previously reported data.[3]

2-(2-Chlorophenyl)pyridine (12)[4]

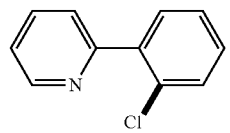

NCS (26 mg, 0.19 mmol) and Pd-MWCNT (8 mg, 5 mol %) were added to a solution of 2-phenylpyridine (25 mg, 0.16 mmol) in ACN (1.3 ml). The reaction was heated at 100° C. for 6 h. After cooling to room temperature, it was diluted with EtOAc, filtered through Celite®, Na$_2$SO$_4$ and dried. The crude product was purified by flash chromatography (silica gel, 10% EtOAc/n-hexane) to give the product as a clear liquid (14.5 mg) in 48% yield. Analytical data ($^1$H NMR, $^{13}$C NMR, mass spec) matched the previously reported data.[4]

2-(2-Chlorophenyl)-3-methylpyridine (13)[5]

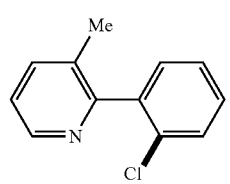

NCS (28 mg, 0.21 mmol) and Pd-MWCNT (9 mg, 5 mol %) were added to a solution of 3-methyl-2-phenylpyridine (30 mg, 0.18 mmol) in AcOH (1.5 ml). The reaction was heated at 120° C. for 10 min. After cooling to room temperature, it was diluted with EtOAc, washed with brine. The organic layer was filtered through Celite®, Na$_2$SO$_4$ and dried. The crude product was purified by flash chromatography (silica gel, 10% EtOAc/n-hexane) to give the product as clear oil (12 mg) in 34% yield. Analytical data ($^1$H NMR, $^{13}$C NMR, mass spec) matched the previously reported data.[5]

10-Bromobenzo[h]quinolone (14)[1]

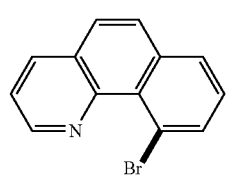

NBS (37 mg, 0.21 mmol) and Pd-MWCNT (7 mg, 5 mol %) were added to a solution of benzo[h]quinoline (25 mg, 0.14 mmol) in ACN (1.2 ml). The reaction was heated at 100° C. for 1.5 h. After cooling to room temperature, it was diluted with EtOAc, filtered through Celite®, Na$_2$SO$_4$ and dried. The crude product was purified by flash chromatography (silica gel, 10% EtOAc/n-hexane) to give the product as a white solid (27 mg) in 89% yield. Analytical data ($^1$H NMR, $^{13}$C NMR, mass spec) matched the previously reported data.[1]

(E)-8-Bromo-3,4-dihydronaphthalen-1(2H)-one O-methyl oxime (15)[5]

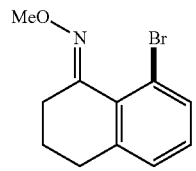

15

NBS (106 mg, 0.60 mmol) and Pd-MWCNT (30 mg, 5 mol %) were added to a solution of (E)-3,4-dihydronaphthalen-1(2H)-one O-methyl oxime (100 mg, 0.57 mmol) in AcOH (4.7 ml). The reaction was heated at 120° C. for 5 h. After cooling to room temperature, it was diluted with EtOAc, washed with brine. The organic layer was filtered through Celite®, Na$_2$SO$_4$ and dried. The crude product was purified by flash chromatography (silica gel, 5% EtOAc/n-hexane) to give the product as yellow oil (43 mg) in 30% yield. Analytical data ($^1$H NMR, $^{13}$C NMR, mass spec) matched the previously reported data.[5]

2-(2-Bromophenyl)pyridine (16)[3]

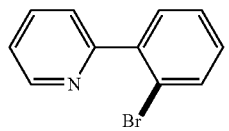

16

NBS (34 mg, 0.19 mmol) and Pd-MWCNT (8 mg, 5 mol %) were added to a solution of 2-phenylpyridine (25 mg, 0.16 mmol) in ACN (1.3 ml). The reaction was heated at 100° C. for 6 h. After cooling to room temperature, it was diluted with EtOAc, filtered through Celite®, Na$_2$SO$_4$ and dried. The crude product was purified by flash chromatography (silica gel, 10% EtOAc/n-hexane) to give the product as yellow oil (12.2 mg) in 32% yield. Analytical data ($^1$H NMR, $^{13}$C NMR, mass spec) matched the previously reported data.[3]

2-(2-Bromophenyl)-3-methylpyridine (17)[5]

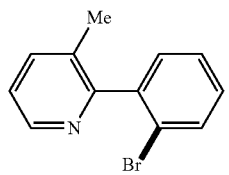

17

NBS (38 mg, 0.21 mmol) and Pd-MWCNT (9 mg, 5 mol %) were added to a solution of 3-methyl-2-phenylpyridine (30 mg, 0.18 mmol) in AcOH (1.5 ml). The reaction was heated at 120° C. for 10 min. After cooling to room temperature, it was diluted with EtOAc, washed with brine. The organic layer was filtered through Celite®, Na$_2$SO$_4$ and dried. The crude product was purified by flash chromatography (silica gel, 10% EtOAc/n-hexane) to give the product as clear oil (20 mg) in 46% yield. Analytical data ($^1$H NMR, $^{13}$C NMR, mass spec) matched the previously reported data.[5]

REFERENCES FOR REACTIONS OF EXAMPLES 1 AND 2

1. *J. Am. Chem. Soc.* 2004, 126(8), 2300-2301.
2. *ACS Chem. Neurosci.* 2013, 4(1), 96-109.
3. *Tetrahedron* 2006, 62, 11483-11498.
4. *J. Am. Chem. Soc.* 2010, 132(41), 14530-14536.
5. *Org. Lett.* 2006, 8(12), 2523-2526.

Figure 10:
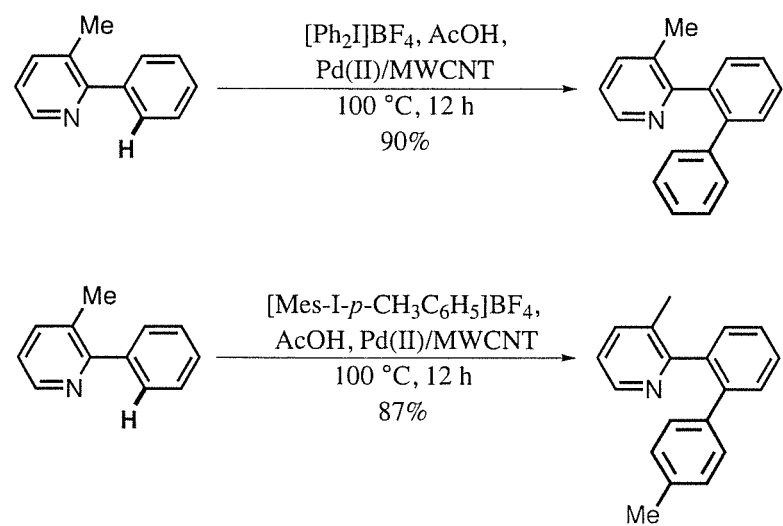
FIG. 10. Exemplary reactions of the oxidative C—H to C—C transformation using the solid-supported Pd(II)/MW-CNT catalyst.

Example 3. Selective N-Chelation-Directed C—H Activation Reactions Catalyzed by Solid-Supported Pd(II) on Multi-Walled Carbon Nanotubes (MWCNT): C—H to C—C Transformation Exemplary reactions of the oxidative C—H to C—C transformation using the solid-supported Pd(II)/MWCNT catalyst were also carried out (FIG. 10). Treatment of 3-methyl-2-phenylpyridine with Pd(II)/MWCNT and [Ph$_2$I] BF$_4$ in acetic acid at 100° C. for 12 h afforded the desired 2-([1,1'-biphenyl]-2-yl)-3-methylpyridine in 90% yield (FIG. 10), comparable to the previously reported yield of 88% with a homogeneous catalyst. Similarly, treatment of 3-methyl-2-phenylpyridine with Pd(II)/MWCNT and [Mes-I-p-CH$_3$C$_6$H$_5$]BF$_4$ in acetic acid at 100° C. for 12 h afforded the desired 2-([1,1'-biphenyl]-2-yl)-3-methylpyridine in 87% yield (FIG. 10), comparable to the previously reported yield of 84% with a homogeneous catalyst.

This Example demonstrates that, in addition to C—O and C-halogen reactions, the solid-supported Pd(II)/MWCNT can catalyze N-chelation-directed C—H to C—C activation reactions. The solid-supported Pd(II)/MWCNT also offers the advantages of ease of removal by filtration and low levels of residual palladium metal contamination in the products. This catalyst can also be utilized in other N-chelation-directed C—H activation reactions.

Reactions for Example 3

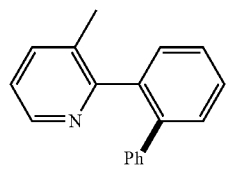

Substrate 3-methyl-2-phenylpyridine (15 mg, 0.089 mmol), Pd-MWCNT (4.7 mg, 5 mol %) and [Ph$_2$I]BF$_4$ (38 mg, 0.102 mmol) were added to AcOH (0.74 ml). The reaction was heated at 100° C. for 12 h. After cooling to room temperature, it was diluted with DCM, washed with saturated aqueous NaHCO$_3$ and brine. The organic layer was filtered through celite, Na$_2$SO$_4$ and dried. The crude product was purified by flash chromatography (silica gel, 5% EtOAc/DCM) to give the product (19.5 mg) in 90% yield. Analytical data ($^1$H NMR, $^{13}$C NMR, mass spec) matched the previously reported data. (Ref: Organic Letters, 2009, 11(15), 3174-3177; J. AM. CHEM. SOC. 2005, 127, 7330-7331)

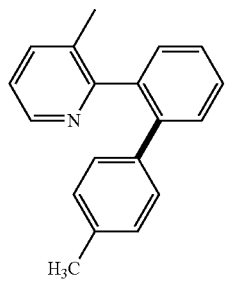

Substrate 3-methyl-2-phenylpyridine (15 mg, 0.089 mmol), Pd-MWCNT (4.7 mg, 5 mol %) and [Mes-I-p-CH$_3$C$_6$H$_5$]BF$_4$ (43 mg, 0.102 mmol) were added to AcOH (0.81 ml). The reaction was heated at 100° C. for 12 h. After cooling to room temperature, it was diluted with DCM, washed with saturated aqueous NaHCO$_3$ and brine. The organic layer was filtered through celite, Na$_2$SO$_4$ and dried. The crude product was purified by flash chromatography (silica gel, 30% EtOAc/n-hexane) to give the product (20 mg) in 87% yield. Analytical data ($^1$H NMR, $^{13}$C NMR, mass spec) matched the previously reported data. (Ref: Organic Letters, 2009, 11(15), 3174-3177; J. AM. CHEM. SOC. 2005, 127, 7330-7331)

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

It is to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

We claim:

1. A method for regioselectively or regiospecifically producing functionalized aryl or heteroaryl compounds by oxidative N-chelation-directed C—H activation, comprising the steps of:
 combining
 i) an aryl or heteroaryl compound containing a) a C—H group and b) a second atom capable of forming a Pd(II) chelate with C of the C—H group after loss of H;
 ii) a solid-supported Pd(II) catalyst selected from the group consisting of Pd(II)/MWCNT, Pd(II)/SWCNT and Pd(II)/graphene; and
 iii) an oxidant comprising an atom or functional group that can replace H of the C—H group in the aryl or heteroaryl compound,
 wherein said combining is performed under conditions wherein
  a) H is lost from the C—H group and C of the C—H group and the second atom chelate Pd(II) of the solid-supported Pd(II) catalyst to form a first Pd(II) chelation adduct;
  b) the atom or functional group is lost from the oxidant species and Pd(II) of the first chelation adduct is oxidized to form a second Pd(IV) chelation adduct in which Pd(IV) is chelated by the second atom, the C of the C—H group and the atom or functional group of the oxidant species; and
  c) the second Pd(IV) chelation adduct undergoes reductive elimination to
   1) produce a functionalized aryl or heteroaryl compound comprising the atom or functional group, and
   2) regenerate Pd(II).

2. The method of claim 1 further comprising the steps of recovering said solid-supported Pd(II) catalyst after said separating step; and
 repeating said steps of combining and separating using at least some of said solid-supported Pd(II) catalyst recovered in said recovering step.

3. The method of claim 1 wherein said aryl or heteroaryl compound and said oxidant each contain at least one aryl or heteroaryl moiety.

4. The method of claim 1 wherein said aryl or heteroaryl compound and said oxidant each contain at least one pyridine.

5. The method of claim 1 wherein said aryl or heteroaryl compound and said oxidant each contain at least one phenyl.

6. The method of claim 1 wherein said aryl or heteroaryl compound and said oxidant each contain at least one cycloalkyl.

7. The method of claim 1 wherein said aryl or heteroaryl compound and said oxidant each contain at least a second phenyl.

8. The method of claim 1 wherein said aryl or heteroaryl compound and said oxidant each contain at least one pyridine.

9. The method of claim 1 wherein said functional group is a halogen.

10. The method of claim 1 wherein said functional group is a alkyl or aryl moiety.

11. The method of claim 1 wherein said functional group is an ether or ester.

12. The method of claim 11 wherein said functional group is an ether OR, where R is a alkyl or alkaryl moiety of 1 to 25 carbons.

13. The method of claim 1, wherein the C of the C—H group is $sp^2$ or $sp^3$ hybridized.

14. The method of claim 1, wherein the second atom is separated from the C of the C—H group by 2 to 4 atoms.

15. The method of claim 1, wherein the first Pd(II) chelation adduct is 5-, 6- or 7-membered palladacycle.

16. The method of claim 1, wherein the method is regiospecific.

17. The method of claim 1, wherein the atom or functional group of the oxidant species is not fluorine.

18. The method of claim 1, wherein the atom or functional group of the oxidant species is Cl, Br or I.

* * * * *